US012679859B2

(12) United States Patent
Matsusako et al.

(10) Patent No.: US 12,679,859 B2
(45) Date of Patent: Jul. 14, 2026

(54) SOPHOROLIPID-CONTAINING COMPOSITION HAVING EXCELLENT HANDLEABILITY

(71) Applicant: SARAYA CO., LTD., Osaka (JP)

(72) Inventors: Takuya Matsusako, Kashiwara (JP); Michiaki Araki, Kashiwara (JP); Yoshihiko Hirata, Kashiwara (JP)

(73) Assignee: SARAYA CO., LTD., Osaka (JP)

( * ) Notice: Subject to any disclaimer, the term of this patent is extended or adjusted under 35 U.S.C. 154(b) by 582 days.

(21) Appl. No.: 18/040,309

(22) PCT Filed: Aug. 5, 2021

(86) PCT No.: PCT/JP2021/029100

§ 371 (c)(1),
(2) Date: Mar. 21, 2023

(87) PCT Pub. No.: WO2022/030577

PCT Pub. Date: Feb. 10, 2022

(65) Prior Publication Data

US 2023/0279038 A1 Sep. 7, 2023

(30) Foreign Application Priority Data

Aug. 5, 2020 (JP) ................................ 2020-133408

(51) Int. Cl.
*C12P 7/64* (2022.01)
*C07H 15/04* (2006.01)
*C12P 19/44* (2006.01)

(52) U.S. Cl.
CPC ................ *C07H 15/04* (2013.01); *C12P 7/64* (2013.01); *C12P 19/44* (2013.01)

(58) Field of Classification Search
CPC .................................. C12P 7/64; C12P 19/44
USPC ........................................................ 435/74
See application file for complete search history.

(56) References Cited

U.S. PATENT DOCUMENTS 8,664,373 B2 * 3/2014 Yanagisawa ............ C12P 19/44
536/18.2
2011/0237531 A1 9/2011 Yanagisawa et al.
2015/0112049 A1 4/2015 Hirata et al.
2017/0143753 A1 5/2017 Gross et al.

FOREIGN PATENT DOCUMENTS

JP 2002-045195 A 2/2002
JP 2003-009896 A 1/2003
JP 2008-247845 A 10/2008
JP 2014-140383 A 8/2014
JP 2015-100290 A 6/2015
WO WO 2010/050413 A1 5/2010

OTHER PUBLICATIONS

Zerhusen et al., European Journal of Lipid Science and Technology, 2020, vol. 122(1), 1900110. (Year: 2020).*
Ashby et al., "Property Control of Sophorolipids: Influence of Fatty Acid Substrate and Blending," *Biotechnol. Lett.*, 30(6): 1093-1100 (2008).
Cooper et al., "Production of a Biosurfactant from *Torulopsis bombicola*," *Appl. Environ. Microbiol.*, 47(1): 173-176 (1984).
Van Bogaert et al., "Microbial Production and Application of Sophorolipids," *Appl. Microbiol. Biotechnol.*, 76(1): 23-34 (2007).
Japan Patent Office, International Search Report in International Patent Application No. PCT/JP2021/029100 (Oct. 19, 2021).
Samtani et al., "Fermentative Production of Sophorolipid and Purification by Adsorption Chromatography," Tenside Surfactants Detergents, 55(6): 467-476 (2018).
Zerhusen et al., "Microbial Synthesis of Nonionic Long-Chain Sophorolipid Emulsifiers Obtained from Fatty Alcohol and Mixed Lipid Feeding," European Journal of Lipid Science and Technology, 122(1): 1900110 (2020).
European Patent Office, Extended European Search Report in European Patent Application No. 21852176.3 (Jun. 11, 2025).
Japan Patent Office, International Preliminary Report on Patentability in International Patent Application No. PCT/JP2021/029100 (Nov. 4, 2022).

* cited by examiner

*Primary Examiner* — Traviss C McIntosh, III
(74) *Attorney, Agent, or Firm* — Leydig, Voit & Mayer, Ltd.

(57) ABSTRACT

The present invention provides a sophorolipid (SL)-containing composition with excellent handleability and a method for producing the sophorolipid-containing composition. The SL-containing composition according to the present invention includes the following characteristics: (A) the content of lactonic SL being 45 to 81 mass % of the total amount of the SL taken as 100 mass %, and (B) the content of oleic acid-diacetyl lactonic SL being 95 mass % or lower of the total amount of the lactonic SL taken as 100 mass %.

4 Claims, No Drawings

SOPHOROLIPID-CONTAINING COMPOSITION HAVING EXCELLENT HANDLEABILITY

TECHNICAL FIELD

The present invention relates to a sophorolipid-containing composition with excellent handleability, and a production method for the sophorolipid-containing composition.

BACKGROUND ART

Biosurfactants ("BS"), which are surfactants of biological origin, are known to be biodegradable and safe. Sophorolipids ("SL"), which are glycolipid-type BS, are fermentation products obtained from fermentation by yeast. SL can be easily produced, for example, by inoculating yeast on a liquid medium supplemented with a carbon source such as a saccharide (e.g., glucose) and vegetable oil and fat, and stirring the medium while aerating it at a mild temperature under pressure. Because of their higher productivity (e.g., about 100 g/L) than other BS, sophorolipids appear to be suitable for production on an industrial scale.

However, to produce a fermentation product in large quantities on an industrial scale, one challenge is to efficiently recover the target product from a culture product obtained at the end of culture. SL is produced in a solubilized form in a culture broth depending on the culture conditions. In this case, SL must be extracted from the culture broth, for example, by using an organic solvent or isolated by column chromatography (see, for example, NPL 1, NPL 2, and PTL 1), which imposes a burden on the environment and operators. SL may also solidify at a low temperature depending on the culture conditions. Removing a solidified SL from a culture tank is difficult, requiring, for example, the addition of warm water or heating the culture tank. This requires increased production energy and also increases the work process and the workload on operators.

There are many known production methods for SL. For example, PTL 2 proposes mixing a fatty acid with a lipid (vegetable oil) as a hydrophobic substrate in a culture medium with the aim of obtaining SL in a large amount at a high yield using *Candida* yeast. Additionally, PTL 3 discloses that in a culture method for producing a large amount of lactonic SL with strong antibacterial and antifungal activity, controlling the amount of oxygen supplied to the medium increases the molar ratio of produced diacetyl lactonic SL, and that increasing the molar ratio of diacetyl lactonic SL to 80% or higher makes it simple to obtain SL in the form of a solid that is easy to handle.

CITATION LIST

Patent Literature

PTL 1: JP2014-140383A
PTL 2: JP2002-45195A
PTL 3: WO2010/050413A
PTL 4: JP2003-9896A

Non-Patent Literature

NPL 1: D. G. Cooper and D. A. Paddock, Appl. Environ. Microbiol., 47, 173-176 (1984)
NPL 2: R. D. Ashby, D. K. Y. Solaiman and T. A. Foglia, Biotechnol. Lett., 30, 1093-1100, 2008

SUMMARY OF INVENTION

Technical Problem

An object of the present invention is to provide a technique of improving the handleability of a composition containing SL ("SL-containing composition" below). Specifically, an object of the present invention is to provide an SL-containing composition with excellent handleability, and a method for producing the SL-containing composition. The term "handleability" includes a sedimentation property and/or fluidity. Specifically, an object of the present invention is to provide an SL-containing composition that has a sedimentation property, and that can be easily separated or recovered from a culture product by allowing for sedimentation in the culture product at the end of culture; and to provide a method for producing the SL-containing composition. Another object of the present invention is to provide an SL-containing composition that does not solidify at a low temperature (−5° C.) and that has fluidity, and to provide a method for producing the SL-containing composition.

Solution to Problem

The present inventors conducted extensive research to achieve the objects and found that an SL-containing composition obtained by culturing an SL-producing yeast in a medium containing vegetable oil and a fatty acid in a specific ratio has an excellent sedimentation property. The inventors also confirmed that the SL-containing composition contains lactonic SL and oleic acid-diacetyl lactonic SL in a predetermined ratio. Additionally, the inventors confirmed that the SL-containing composition does not solidify at a temperature of −5° C. and has fluidity at low temperature when the water content is adjusted to 35 to 70 mass %. The present invention was completed as a result of further research based on these findings and includes the following embodiments.

(I) Sophorolipid (SL)-Containing Composition (I-1) An SL-containing composition including the following characteristics:

- (A) the content of lactonic SL being 45 to 81 mass % of the total amount of the SL taken as 100 mass %, and
- (B) the content of oleic acid-diacetyl lactonic SL being 95 mass % or lower of the total amount of the lactonic SL taken as 100 mass %.

(I-2) The SL-containing composition according to (I-1), comprising the following characteristic:

- (C) the content of a hexane extract being 6 mass % or lower on a dry-weight basis.

(I-3) The SL-containing composition according to (I-1) or (I-2), comprising the following characteristic:

- (D) the water content being 55 mass % or lower.

(I-4) The SL-containing composition according to any one of (I-1) to (I-3), further comprising the following characteristic (E) or (F), or both:

- (E) the content of acidic SL being 10 to 50 mass % of the total amount of the SL taken as 100 mass %, and
- (F) the content of dimeric SL being 0.1 to 40 mass % of the total amount of the SL taken as 100 mass %.

(I-5) The SL-containing composition according to any one of (I-1) to (1-4), wherein after the SL-containing composition is adjusted to have a water content of 50 mass % and allowed to stand at −5° C. for 72 hours, the SL-containing composition has a viscosity of 1490 mPa·s or higher at a product temperature of −5° C. as measured with a TVB-10M viscometer for a measurement time of 1 minute.

(I-6) The SL-containing composition according to any one of (I-1) to (I-5), comprising the following characteristic:

(A) the content of lactonic SL being 58 to 81 mass % of the total amount of the SL taken as 100 mass %.

(I-7) The SL-containing composition according to (I-6), comprising the following characteristic:

(D) the water content being 45 mass % or lower.

(I-8) The SL-containing composition according to (I-6) or (I-7), further comprising the following characteristic (E) or (F), or both:

(E) the content of acidic SL being 15 to 25 mass of the total amount of the SL taken as 100 mass %, and (F) the content of dimeric SL being 5 to 25 mass % of the total amount of the SL taken as 100 mass %.

(I-9) The SL-containing composition according to any one of (I-6) to (I-8), wherein after the SL-containing composition is adjusted to have a water content of 50 mass % and allowed to stand at −5° C. for 72 hours, the SL-containing composition has a viscosity of 8180 mPa·s or higher at a product temperature of −5° C. as measured with a TVB-10M viscometer for a measurement time of 1 minute.

(II) Method for Producing SL-Containing Composition 1

(II-1) A method for producing an SL-containing composition comprising the following characteristics (A) and (B), or (A) to (C):

(A) the content of lactonic SL being 45 to 81 mass % of the total amount of the SL taken as 100 mass %, (B) the content of oleic acid-diacetyl lactonic SL being 95 mass % or lower of the total amount of the lactonic SL taken as 100 mass %, and (C) the content of a hexane extract being 6 mass % or lower on a dry-weight basis;

the method comprising culturing an SL-producing yeast in a medium containing a hydrophobic substrate and a hydrophilic substrate, wherein the hydrophobic substrate contains only a fatty acid, or the hydrophobic substrate contains a fatty acid and a vegetable oil with a melting point of 30° C. or lower, and the proportion of a free fatty acid is 20 mass % or higher, preferably 30 mass % or higher, of the total amount of the fatty acid taken as 100% contained in the medium, or when the hydrophobic substrate contains the vegetable oil with a melting point of 30° C. or lower, the proportion of the free fatty acid is 20 mass % or higher, preferably 30 mass % or higher, of the total amount of the fatty acid and the vegetable oil taken as 100 mass % in the medium.

(II-2) The method according to (11-1), wherein a culture product at an early stage of culture has a pH of 4 to 5.

(II-3) The method according to (II-2), wherein the pH of the culture product is not controlled during a culture period.

(II-4) The method according to any one of (II-1) to (II-3), wherein conditions for aerated agitation culture during the culture period are set such that the amount of oxygen supplied to the culture product in terms of apparent oxygen mass transfer coefficient ($k_La$) is 145l/hr or higher, preferably 200l/hr or higher, more preferably 500l/hr or higher, and, without any limitation, 1200l/hr or lower.

(II-5) The method according to any one of (II-1) to (II-4), wherein the SL-containing composition further comprises the following characteristic (E) or (F), or both:

(E) the content of acidic SL being 10 to 50 mass % of the total amount of the SL taken as 100 mass %, and (F) the content of dimeric SL being 0.1 to 40 mass % of the total amount of the SL taken as 100 mass %.

(II-6) The method according to any one of (II-1) to (II-5), wherein after the SL-containing composition is adjusted to have a water content of 50 mass % and allowed to stand at −5° C. for 72 hours, the SL-containing composition has a viscosity of 1490 mPa·s or higher at a product temperature of −5° C. as measured with a TVB-10M viscometer for a measurement time of 1 minute.

(III) Method for Producing SL-Containing Composition 2

(III-1) A method for producing an SL-containing composition comprising the following characteristics (A) and (B), or (A) to (C):

(A) the content of lactonic SL being 45 to 81 mass %, preferably 55 to 81 mass %, of the total amount of the SL taken as 100 mass %, (B) the content of oleic acid-diacetyl lactonic SL being 95 mass % or lower of the total amount of the lactonic SL taken as 100 mass %, and (C) the content of a hexane extract being 6 mass % or lower on a dry-weight basis;

the method comprising culturing an SL-producing yeast in a medium containing a hydrophobic substrate and a hydrophilic substrate, wherein the hydrophobic substrate contains only a vegetable oil with a melting point of 30° C. or lower, and the pH of a culture product during the culture is adjusted to 4.5 to 5.

(III-2) The method according to (III-1), wherein conditions for aerated agitation culture during a culture period are set such that the amount of oxygen supplied to the culture product in terms of apparent oxygen mass transfer coefficient ($k_La$) is 200 l/hr or higher, and, without any limitation, 1200l/hr or lower.

(III-3) The method according to (III-1) or (III-2), wherein the SL-containing composition further comprises the following characteristic (E) or (F), or both:

(E) the content of acidic SL being 10 to 50 mass %, preferably 15 to 30 mass %, of the total amount of the SL taken as 100 mass %, and (F) the content of dimeric SL being 0.1 to 40 mass %, preferably 1 to 30 mass %, of the total amount of the SL taken as 100 mass %.

(III-4) The method according to any one of (III-1) to (III-3), wherein after the SL-containing composition is adjusted to have a water content of 50 mass % and allowed to stand at −5° C. for 72 hours, the SL-containing composition has a viscosity of 1490 mPa·s or higher, preferably 8000 mPa·s or higher, at a product temperature of −5° C. as measured with a TVB-10M viscometer for a measurement time of 1 minute.

(IV) Method for Producing SL-Containing Composition 3

(IV-1) A method for producing an SL-containing composition comprising the following characteristics (A) and (B), or (A) to (C):

(A) the content of lactonic SL being 45 to 81 mass %, preferably 50 to 80 mass %, of the total amount of the SL taken as 100 mass %, (B) the content of oleic acid-diacetyl lactonic SL being 95 mass % or lower of the total amount of the lactonic SL taken as 100 mass %, and (C) the content of a hexane extract being 6 mass % or lower on a dry-weight basis;

the method comprising culturing an SL-producing yeast in a medium containing a hydrophobic substrate and a hydrophilic substrate, wherein the hydrophobic substrate contains only a vegetable oil with a melting point of 30° C. or lower, or the hydrophobic substrate contains a vegetable oil with a melting point of 30° C. or lower and a fatty acid, the proportion of a free fatty acid is 0 to lower than 20 mass % of the total amount of the vegetable oil with a melting point of 30° C. or lower taken as 100 mass % contained in the medium, or when the hydrophobic substrate contains the fatty acid, the proportion of the free fatty acid is 0 to lower than 20 mass % of the total amount of the vegetable oil with a melting point of 30° C. or lower and the fatty acid taken as 100 mass % contained in the medium, and conditions for aerated agitation culture during a culture period are set such that the amount of oxygen supplied to a culture product in terms of apparent oxygen mass transfer coefficient ($k_La$) is 145l/hr or lower.

(IV-2) The method according to (IV-1), wherein the culture product at an early stage of culture has a pH of 4 to 5.

(IV-3) The method according to (IV-2), wherein the pH of the culture product is not controlled during the culture period.

(IV-4) The method according to any one of (IV-1) to (IV-3), wherein the SL-containing composition further comprises the following characteristic (E) or (F), or both:

(E) the content of acidic SL being 10 to 50 mass %, preferably 10 to 20 mass %, of the total amount of the SL taken as 100 mass %, and (F) the content of dimeric SL being 0.1 to 40 mass %, preferably 5 to 30 mass %, of the total amount of the SL taken as 100 mass %.

(IV-5) The method according to any one of (IV-1) to (IV-4), wherein after the SL-containing composition is adjusted to have a water content of 50 mass % and allowed to stand at −5° C. for 72 hours, the SL-containing composition has a viscosity of 1490 mPa·s or higher, preferably 3000 mPa·s or higher at a product temperature of −5° C. as measured with a TVB-10M viscometer for a measurement time of 1 minute.

Advantageous Effects of Invention

The present invention produces and provides an SL-containing composition excellent in sedimentation property and handleability. The present invention also produces and provides an SL-containing composition that does not solidify at a low temperature of −5° C. and that has excellent fluidity.

DESCRIPTION OF EMBODIMENTS (I) Sophorolipid (SL)-Containing Composition (1) Sophorolipid (SL)

Sophorolipids (SL) are glycolipids consisting of sophorose or sophorose having some hydroxy groups acetylated, and a hydroxy fatty acid. Sophorose is a carbohydrate consisting of two bound glucose molecules (P1-2). Hydroxy fatty acids are fatty acids having a hydroxy group. SL is broadly classified into acidic SL and lactonic SL. Acidic SL is a sophorolipid in which the carboxy group of the hydroxy fatty acid is free. Lactonic SL is a sophorolipid in which the carboxy group of the hydroxy fatty acid is bound to the sophorose in the molecule. Sophorolipids obtained from a species of yeast (SL-producing yeast) through fermentation are usually a mixture of acidic SL represented by the following formula (1) and lactonic SL represented by the following formula (2), and are obtained as a collection of 30 or more types of structural homologues, such as those having different fatty acid chain lengths ($R_2$), those acetylated or protonated at the 6'-position ($R_3$) and the 6"-position ($R_4$) of the sophorose, and those esterified at one of the 3'-, 4'-, 2"-, 3"-, and 4"-positions ($R_5$) of the sophorose.

(1)

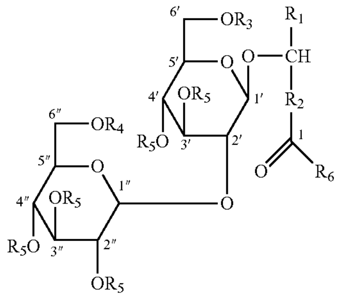

Acidic SL

In formula (1), $R_1$ represents a hydrogen atom or a methyl group;

$R_3$ and $R_4$ are the same or different and represent a hydrogen atom or an acetyl group;

all $R_5$s are hydrogen atoms, or one of the five $R_5$s is a saturated or unsaturated fatty acid residue that may have hydroxy, and the remaining four $R_5$s are all a hydrogen atom;

$R_2$ is a saturated aliphatic hydrocarbon chain, or an unsaturated aliphatic hydrocarbon chain having at least one double bond optionally substituted with one or more substituents; and $R_6$ is a hydroxy group.

In the present specification, acidic sophorolipids in which all $R_5$s are a hydrogen atom in formula (1) are referred to as "acidic SLa," and the remaining acidic sophorolipids are referred to as "acidic SLb." When both are referred to collectively without any distinction, they are referred to as "acidic SL." Acidic SL is a monomer and may be referred to as "monomeric acidic SL" as opposed to the dimeric SL described later.

(2)

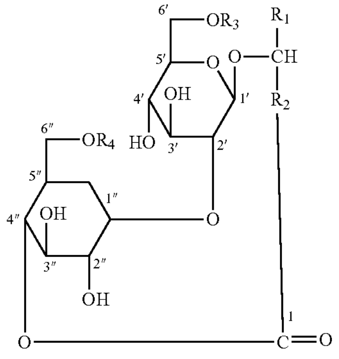

Lactonic SL

In formula (2), R, to $R_4$ are as defined in formula (1).

In the present specification, lactonic sophorolipids in which $R_3$ and $R_4$ are both an acetyl group in formula (2) are referred to as "diacetyl lactonic SL." When sophorolipids are referred to collectively without distinction as to whether an acetyl group is present, they are referred to as "lactonic SL." Lactonic SL is a monomer and may be referred to as "monomeric lactonic SL" as opposed to the dimeric SL described later.

The SL obtained through fermentation by using an SL-producing yeast may contain a dimer composed of the acidic SL represented by formula (1) in which one $R_5$ is a saturated or unsaturated fatty acid residue that may have hydroxy bound at its $R_5$ at the C-1 position to the acidic SL represented by the following formula (3) at one of $R_7$s to form a single bond.

(3)

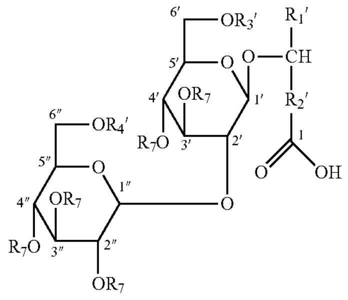

Dimeric SL

In formula (3), $R_{1'}$ is a hydrogen atom or a methyl group;

$R_{3'}$ and $R_{4'}$ are the same or different and represent a hydrogen atom or an acetyl group;

$R_{2'}$ is a saturated aliphatic hydrocarbon chain, or an unsaturated aliphatic hydrocarbon chain having at least one double bond optionally substituted with one or more substituents; and one $R_7$ is bound to $R_6$ of the acidic SL represented by formula (1) to form a single bond, and the remaining $R_7$s are all a hydrogen atom.

In formulas (1) to (3), the number of carbons in the saturated or unsaturated aliphatic hydrocarbon chain represented by $R_2$ or $R_{2'}$ is not limited, but is typically, for example, 9 to 20, preferably 9 to 18, more preferably 11 to 16, and particularly preferably 14 to 16. Examples saturated aliphatic hydrocarbon chains include linear or branched alkylene groups, with linear alkylene groups being preferable. Examples of unsaturated aliphatic hydrocarbon chains include alkenylene groups having 1 to 3 double bonds. The unsaturated aliphatic hydrocarbon chain is preferably an alkenylene group having 1 to 2 double bonds, and more preferably an alkenylene group having 1 double bond. There is no limitation to the substituents of the saturated or unsaturated aliphatic hydrocarbon chain represented by $R_2$ or $R_{2'}$. Examples of substituents include halogen atoms, hydroxy groups, lower ($C_{1-6}$) alkyl groups, halo-lower ($C_{1-6}$) alkyl groups, hydroxy lower ($C_{1-6}$) alkyl groups, and halo-lower ($C_{1-6}$) alkoxy groups. Examples of halogen atoms or halogen atoms bound to alkyl or alkoxy groups include a fluorine atom, a chlorine atom, a bromine atom, and an iodine atom.

Examples of saturated fatty acid residues represented by $R_5$ in formula (1) include $C_{12-20}$ linear fatty acid residues (lauric acid residue, myristic acid residue, pentadecylic acid residue, palmitic acid residue, margaric acid residue, stearic acid residue, and arachidic acid residue), preferably $C_{14-20}$, more preferably $C_{16-20}$, even more preferably $C_{16-18}$ linear fatty acid residues, and particularly preferably $C_{16}$ palmitic acid residues and $C_{18}$ stearic acid residues. Examples of unsaturated fatty acid residues include $C_{12-20}$ linear fatty acid residues having 1 to 3 double bonds. The number of double bonds is preferably 1 to 2, and more preferably 1. The number of carbon atoms is preferably 16 to 20, more preferably 16 to 18, and particularly preferably 18. Examples of preferable unsaturated fatty acid residues include a $C_{16}$ palmitoleic acid residue having one double bond; a $C_{18}$ oleic acid residue having one double bond or a vaccenic acid residue having one double bond (preferably oleic acid residue); a $C_{18}$ linoleic acid residue having two double bonds; a $C_{18}$ linolenic acid residue (9, 12, 15), a linolenic acid residue (6, 9, 12), and an eleostearic acid residue each having three double bonds; and a $C_{20}$ linolenic acid residue (9, 12, 15), a linolenic acid residue (6, 9, 12), and an eleostearic acid residue each having two double bonds. More preferably, the unsaturated fatty acid residue is a $C_{16}$ palmitoleic acid residue having one double bond and a $C_{18}$ oleic acid residue having one double bond, particularly preferably a Cis oleic acid residue having one double bond.

These fatty acid residues may or may not have hydroxy. The number of hydroxy groups of a fatty acid residue having hydroxy is 1 or 2, preferably 1. The hydroxy may be present, for example, at the ω-position or ω-1-position in the fatty acid residue. In acidic SL (1), when $R_5$ is a saturated or unsaturated fatty acid residue that may have hydroxy, —$OR_5$ may be present at any of the 3', 4', 2", 3", and 4"-positions of the sophorose ring. More specifically, acidic SL (1) includes SL compounds in which an —$OR_5$ group having $R_5$ that is the fatty acid residue described above is present at one of these positions.

Diacetyl lactonic sophorolipids in which $R_3$ and $R_4$ are both an acetyl group in formula (2) include SL compounds in which $R_1$ is a methyl group, and $R_2$ is a $C_{15}$ alkenylene group having one double bond. Of these SL compounds, in particular, a compound in which $R_2$ is a $C_{15}$ alkenylene group having double bonds at the 8-position and 9-position, with the carbon atom to which R, is bound being the 1-position, is preferable. In the present invention, this compound is referred to as "oleic acid-diacetyl lactonic SL."

Examples of preferable SL-producing yeast include *Candida bombicola*. The *Candida* genus has been renamed the *Starnerella* genus. This yeast is known to produce a significant amount of SL (Canadian Journal of Chemistry, 39, 846 (1961) (note: the *Torulopsis* genus described in the document belongs to the *Candida* genus, but is currently classified into the *Starmerella* genus, as stated above); Applied and Environmental Microbiology, 47, 173 (1984); etc.). *Candida* (*Starmerella*) *bombicola* has been deposited with, and is available from, the American Type Culture Collection (ATCC), which is a bioresource bank (*Candida bombicola* ATCC22214). Other SL-producing yeast species that are known to produce SL and that belong to the *Candida* genus (*Starmerella* genus) are also usable. Examples of such SL-producing yeast species include *Candida magnoliae, Candida gropengisseri, Candida apicola, Candida petrophilum, Candida bogoriensis*, and *Candida* batistae.

(2) SL-Containing Composition

Of the sophorolipids described above, the SL-containing compositions covered by the present invention are those containing at least acidic SL and lactonic SL. Preferably, the SL-containing compositions covered by the present invention are those containing lactonic SL and oleic acid-diacetyl lactonic SL in a predetermined ratio, more preferably those containing acidic SL and dimeric SL in a predetermined ratio. The SL-containing compositions covered by the present invention also include hydrous materials containing water in a predetermined ratio.

Specifically, the SL-containing composition according to the present invention includes the compositions having the following characteristics (A) and (B), or (A) to (C):

(A) the content of lactonic SL being 45 to 81 mass % of the total amount of the SL taken as 100 mass %, (B) the content of oleic acid-diacetyl lactonic SL being 95 mass % or lower of the total amount of the lactonic SL taken as 100 mass %, and (C) the content of a hexane extract being 6 mass % or lower on a dry-weight basis.

For example, the content of lactonic SL is, but is not limited to, preferably 45 to 78 mass %, more preferably 50 to 78 mass % of the total amount of the SL taken as 100 mass %.

For example, the lower limit of the content of oleic acid-diacetyl lactonic SL is, but is not limited to, 10 mass % of the total amount of lactonic SL taken as 100 mass %. For example, the content of oleic acid-diacetyl lactonic SL is preferably within the range of 40 to 95 mass %, more preferably 55 to 95 mass %.

For example, the content of a hexane extract is, but is not limited to, 6 mass % or lower, preferably 0 to 5 mass %, more preferably 0 to 2.2 mass % on a dry-weight basis. The content of a hexane extract in the SL-containing composition can be determined from the weight of a dry product obtained from the SL-containing composition by extraction with n-hexane at room temperature (20±5° C.). The details are described in the Examples section below.

The SL-containing composition according to the present invention also includes the composition having the following characteristic:

(D) the water content being 55 mass % or lower.

The SL-containing composition according to the present invention may be a dry product free of water, or a hydrous material, which contains water. The SL-containing composition is preferably a hydrous material containing water in an amount of 52 mass % or lower. For example, the lower limit of the water content is, but is not limited to, 30 mass %, preferably 35 mass % or higher, more preferably 40 mass % or higher. The water content in the SL-containing composition (hydrous material) is preferably 35 to 55 mass %, more preferably 40 to 55 mass %. The water content of the SL-containing composition can be determined from the difference in weight of the SL-containing composition before and after the SL-containing composition is subjected to dry treatment at 105° C. for 3 hours. The details are described in the Examples section below.

The SL-containing composition according to the present invention further includes the composition having the following characteristics in addition to the characteristics (A) and (B), (A) to (C), or (A) to (D) described above:

(E) the content of acidic SL being 10 to 50 mass % of the total amount of the SL taken as 100 mass %, and (F) the content of dimeric SL being 0.1 to 40 mass % of the total amount of the SL taken as 100 mass %.

For example, the content of acidic SL is, but is not limited to, preferably 13 to 50 mass %, more preferably 15 to 46 mass % of the total amount of the SL taken as 100 mass %. For example, the content of the dimeric SL is, but is not limited to, preferably 0.5 to 30 mass %, more preferably 1 to 30 mass % of the total amount of the SL taken as 100 mass %.

The characteristics (A), (B), (E), and (F) described above can be calculated from the peak area of each sophorolipid obtained by diluting the target SL-containing composition with ethanol (99.5 v %) such that a dry residue is about 1%, and subjecting the prepared ethanol-diluted product to high-performance liquid chromatography (HPLC) under the conditions shown in Table 1 below. The method for calculating the dry residue is described in the Examples section below.

TABLE 1

| Conditions for HPLC Analysis |
|---|
| System: Shimadzu Corporation, Prominence-i |
| Column: Inertsil ODS-3 (4.6 mm × 250 mm) |
| Column Temperature: 40° C. |
| Mobile Phase: (A) Distilled Water, (B) Methanol containing 0.1 vol % of formic acid |
| Gradient: 0.1 min → 60 min: (A) 30% + (B) 70% → (B) 100% |
| 60 min → 70 min: (B) 100% → (A) 30% + (B) 70% |
| Flow Rate: 1.0 mL/min |
| Sample Preparation Liquid: Ethanol (99.5 v %) |
| Injection Amount: 10 μL |
| Detector: Evaporative Light Scattering Detector (Shimadzu Corporation: ELSD-LT II) |
| Detector Temperature: 40° C. |
| Gain: 5 |
| Gas Pressure: 350 kPa ($N_2$ gas) |

In HPLC under the conditions shown in Table 1, monomeric acidic SL elutes in the regions at a retention time of 10 to 23 minutes (acidic SLa) and 45 to 58 minutes (acidic SLb). Monomeric lactonic SL (which contains diacetyl lactonic SL; the same applies below) elutes in the region at a retention time of 23 to 40 minutes. Of the peaks that appear in this region, particularly in the region of 28 to 33 minutes, the peak with the highest intensity is derived from oleic acid-diacetyl lactonic SL. Dimeric SL elutes in the region at a retention time of 58 to 70 minutes.

The mass ratio of acidic SL (acidic SL a, acidic SL b), lactonic SL, and dimeric SL contained in the SL-containing composition can be calculated from the percentage of each peak obtained from the HPLC analysis. Specifically, the sum (100) of the peak areas of individual SLs (acidic SL, lactonic SL, dimeric SL) is assumed to be the total SL amount (100 mass %), and the percentage of the peak area of each SL in the total SL amount is calculated to determine the percentage by mass of each SL.

The percentage of oleic acid-diacetyl lactonic SL in the total amount of lactonic SL 100 mass % can also be calculated from the percentage of each peak obtained from the HPLC analysis.

The SL-containing composition according to the present invention includes a composition having a viscosity of 1490 mPa·s or higher at a product temperature of −5° C. after the SL-containing composition is adjusted to have a water content of 50 mass % and allowed to stand at −5° C. for 72 hours. For example, the viscosity is, but is not limited to, preferably 2000 mPa·s or higher, more preferably 2500 mPa·s or higher. The upper limit of the viscosity is not limited as long as the effects of the present invention are brought about; for example, the upper limit is 221300 mPa·s or lower, preferably 21000 mPa·s or lower.

The viscosity can be measured with a TVB-10M viscometer for a measurement time of 1 minute. The viscometer with the following rotor No. and stirring speed can be used according to the viscosity of the sample to be measured:

TABLE 2

| Measurement Viscosity | Rotor Number | Stirring Speed |
|---|---|---|
| Lower than 2000 mPa · s | M2 or M3 | 60 rpm |
| 2000 to 10000 mPa · s | M4 | 60 rpm |
| 10000 to 20000 mPa · s | M4 | 30 rpm |
| 20000 to 50000 mPa · s | M4 | 12 rpm |
| 50000 to 100000 mPa · s | M4 | 6 rpm |
| 100000 to 200000 mPa · s | M4 | 3 rpm |
| 200000 to 400000 mPa · s | M4 | 1.5 rpm |

The SL-containing composition according to the present invention contains SL in a predetermined amount as described above. The SL-containing composition according to the present invention is not particularly limited in terms of its production method and includes those produced by culturing the SL-producing yeast described later; however, the SL-containing composition according to the present invention has at least the following characteristic such that when the SL-containing composition is adjusted with distilled water to give a water content of about 91.7 mass % and adjusted to have a pH in the acidic range (pH: 2.5 to 3.0), the sophorolipids contained in the composition become insoluble and settle out. The characteristic of the SL-containing composition is referred to as "sedimentation property" in the present invention.

Although the details of the evaluation method for the sedimentation property of the SL-containing composition are described in the Examples section (Physical Properties Evaluation Method, (2-2) Sedimentation Property of SL-containing Composition in Distilled Water), a brief explanation is given below.

25 g of distilled water (product temperature: 20° C.) is added to 5 g of an SL-containing composition (product temperature: 20° C.) that has been adjusted to give 50% of a dry residue so as to dilute the SL-containing composition (water content: about 91.7 mass %). If the diluted product has a pH outside of 2.5 to 3.0, the pH is adjusted to 2.5 to 3.0 with a pH adjuster (e.g., an acid such as hydrochloric acid or sulfuric acid, or an alkaline agent such as sodium hydroxide or potassium hydroxide). The diluted product is mixed with stirring for 10 seconds, and then allowed to stand at 20° C. for 5 minutes, followed by visually confirming whether sediment is present. If obvious sediment (or obvious separation) is observed, the composition is determined to "have a sedimentation property"; otherwise, the composition is determined to "have no sedimentation property."

Specifically, "having a sedimentation property" means that an SL-containing composition contains SL under the conditions that when the composition is adjusted to an acidic diluted product with a water content of about 91.7 mass % (pH: 2.5 to 3.0), the SL becomes insoluble and settles out. The SL-containing composition having such a sedimentation property is considered to be easy to handle in that SL can be insolubilized and allowed to settle out to recover it by a simple method such as diluting the composition with distilled water and/or adjusting the pH to the acidic range.

As described in the Examples (the results of physical properties evaluation of Production Examples 1 to 4) later, the SL-containing composition evaluated as "having a sedimentation property" in the evaluation method is also observed as having an excellent sedimentation property in a culture product in the same manner. Specifically, if an SL-containing composition that has the same composition as that of the SL-containing composition evaluated as "having a sedimentation property" in the evaluation method (the total SL amount, SL composition (%), the percent of oleic acid-diacetyl lactonic SL (%) contained in lactonic SL, or/and the content of the hexane extract) is produced by culturing an SL-producing yeast, the SL-containing composition is assumed to have an excellent sedimentation property in the culture product.

The SL-containing composition according to the present invention also has low-temperature fluidity. Although the details of the evaluation method for low-temperature fluidity of the SL-containing composition are described in the Examples section, a brief explanation is given below.

The SL-containing composition is placed in a container covered with a lid and allowed to stand in the dark at −5° C. for 3 days (72 hours). Then, the container is inverted and visually observed for fluidity of the contents for 30 seconds. If the water content of the SL-containing composition to be measured is not 50 mass %, distilled water is added to adjust the water content to 50 mass %. If visual inspection reveals that the contents have fluidity, the SL-containing composition is considered to "have low-temperature fluidity"; otherwise, the SL-containing composition is considered to "have no low-temperature fluidity."

The SL-containing composition with low-temperature fluidity is considered to be easier to work with and handle than SL-containing compositions with no fluidity that solidify at a low temperature.

(II) Method for Producing SL-Containing Composition

The SL-containing composition according to the present invention can be any having the composition and characteristics described above, and the production method for the SL-containing composition is not particularly limited. Without limitation, for example, the SL-containing composition can be produced by culturing an SL-producing yeast under predetermined conditions by using an aqueous liquid medium containing a hydrophobic substrate and a hydrophilic substrate. In this case, however, the SL-containing compositions covered by the present invention do not include culture products obtained by culture themselves as are ("SL-containing culture product" below).

The hydrophobic substrate has a low affinity for water used as a medium solvent. The types of the hydrophobic substrate preferably include, but are not limited to, fatty acids, and vegetable oils containing fatty acids as constituents. Fatty acids include $C_{6-18}$ saturated or unsaturated fatty acids. These can be used singly, or in a combination of two or more. The hydrophobic substrate is preferably at least one fatty acid selected from the group consisting of $C_{12-18}$ saturated or unsaturated fatty acids, more preferably at least one fatty acid selected from the group consisting of $C_{18}$ saturated fatty acid (palmitic acid) and $C_{18}$ saturated or unsaturated fatty acids (stearic acid, oleic acid, linoleic acid, linolenic acid) fatty acids. Vegetable oils include, but are not limited to, preferably those containing a $C_{12-18}$ saturated or unsaturated fatty acid as the fatty acid component of triglycerides. Vegetable oils include soybean oil, rapeseed oil, cottonseed oil, sunflower oil (high linoleic, high oleic), kapok oil, sesame oil, corn oil, rice oil, peanut oil, safflower oil (high linoleic, high oleic), olive oil, linseed oil, tung oil, castor oil, palm kernel oil, palm olein, palm stearin, and coconut oil. These vegetable oils all have a melting point of 30° C. or lower. These can be used singly, or in a combination of two or more.

The hydrophilic substrate has a high affinity for water used as a medium solvent. The hydrophilic substrate is preferably, but is not limited to, carbohydrates and nitrogen sources necessary for the growth of SL-producing yeast. Carbohydrates include monosaccharides such as glucose, fructose, and galactose, and disaccharides such as sucrose and maltose, with monosaccharides such as glucose being preferable. The type of nitrogen sources includes yeast extracts, peptone, and urea.

In addition to the hydrophobic substrate and the hydrophilic substrate, the medium may optionally contain inorganic salts (e.g., phosphates, magnesium salts, and sodium salts), organic acids (e.g., lactic acid, acetic acid, citric acid, and propionic acid), and vitamins useful for the growth of SL-producing yeast, to the extent that these substances do not interfere with the effects of the present invention.

Although the method for producing an SL-containing composition by using an SL-producing yeast is not limited, the three methods described below (production methods 1 to 3) are preferable.

(1) Production Method 1

Production method 1 includes the step of culturing an SL-producing yeast by using, as a hydrophobic substrate added to a medium for use, at least a fatty acid or a fatty acid and a vegetable oil with a melting point of 30° C. or lower, and using a medium containing a free fatty acid in an amount of 20 mass % or higher of the total amount of the fatty acid taken as 100 mass % contained in the medium or of the total amount of the fatty acid and the vegetable oil with a melting point of 30° C. or lower taken as 100 mass % contained in the medium when the hydrophobic substrate contains the vegetable oil (which are collectively referred to as "the total amount of the fatty acid and the vegetable oil").

The proportion of the free fatty acid in the total amount of the fatty acid and the vegetable oil taken as 100% in the medium is preferably, but is not limited to, 30 mass % or higher. The upper limit is 100 mass % (however, this is only in the case in which no vegetable oil is used, and only a fatty acid is used as a hydrophobic substrate).

In the production method, the pH of the culture product is preferably not controlled during the culture period, except that the pH at the early stage of culture is within the range of 4 to 5. In this case, during the culture period, the pH of the culture product gradually decreases and typically reaches, but is not limited to, around a pH of 3 at the end of the culture.

In the production method, the culture of the SL-producing yeast is preferably performed according to an aerated agitation culture method. The conditions for aerated agitation culture can be set, for example, such that the amount of oxygen supplied to the medium in terms of apparent oxygen mass transfer coefficient ($k_La$) is 145l/hr or higher. The apparent oxygen mass transfer coefficient is preferably 200l/hr or higher, more preferably 500l/hr or higher. The upper limit is, but is not limited to, 1200l/hr or lower. The details of the method for setting the amount of oxygen supplied to the culture product are described in the Examples section (the same applies to the following Production Methods 2 and 3).

A culture product containing SL (SL-containing culture product) can be obtained by performing culture under the conditions described above at 20 to 45° C., preferably 25 to 35° C., for about 4 to 14 days, preferably for about 5 to 7 days. A desired SL-containing composition that provides the effects of the present invention can be prepared and obtained by treating the SL-containing culture product according to a method described later.

(2) Production Method 2

Production method 2 includes the step of culturing an SL-producing yeast by using a vegetable oil with a melting point of 30° C. or lower as a hydrophobic substrate to be added to a medium and by adjusting the pH of the culture product to 4.5 to 5 during the culture period.

The pH of the culture product during the culture period can be adjusted by adding a pH adjuster (e.g., sodium hydroxide or potassium hydroxide) as appropriate, while monitoring the pH of the culture product, although the method is not limited.

In the production method, the culture of the SL-producing yeast is preferably performed according to an aerated agitation culture method. The conditions for aerated agitation culture can be set, for example, such that the amount of oxygen supplied to the medium in terms of apparent oxygen mass transfer coefficient ($k_La$) is higher than 160 l/hr. The apparent oxygen mass transfer coefficient is preferably 200l/hr or higher, more preferably 500l/hr or higher. The upper limit is, but is not limited to, 1200l/hr or lower. A culture product containing SL (SL-containing culture product) can be obtained by performing culture under the conditions described above at 20 to 45° C., preferably 25 to 35° C., for about 4 to 14 days, preferably for about 5 to 7 days. A desired SL-containing composition that provides the effects of the present invention can be prepared and obtained by treating the SL-containing culture product according to a method described later (3) Production Method 3

Production method 3 includes the step of culturing an SL-producing yeast by using, as a hydrophobic substrate added to a medium for use, a vegetable oil with a melting point of 30° C. or lower, or a fatty acid and a vegetable oil with a melting point of 30° C. or lower, and using a medium containing a free fatty acid in an amount of 0 to lower than 20 mass % of the total amount of the vegetable oil with a melting point of 30° C. or lower or of the total amount of the vegetable oil with a melting point of 30° C. or lower and the fatty acid taken as 100 mass % contained in the medium when the hydrophobic substrate contains a fatty acid (which are collectively referred to as "the total amount of the fatty acid and the vegetable oil"), with the conditions for aerated agitation culture being set such that the amount of oxygen supplied to the medium in terms of apparent oxygen mass transfer coefficient ($k_La$) is 145l/hr or lower.

The lower limit of the oxygen mass transfer coefficient is, for example, but is not limited to, 75 l/hr. Preferably, culture is performed under the conditions for aerated agitation culture such that the amount of oxygen supplied to the medium in terms of apparent oxygen mass transfer coefficient ($k_La$) is 100 to 145 l/hr, more preferably 120 to 145 l/hr. In the production method, the pH of the culture product is preferably not controlled during the culture period, except that the pH at the early stage of culture is within the range of 4 to 5. In this case, during the culture period, the pH of the culture product gradually decreases and typically reaches, but is not limited to, around a pH of 3 at the end of the culture.

A culture product containing SL (SL-containing culture product) can be obtained by performing culture under the conditions described above at 20 to 45° C., preferably 25 to 35° C. for about 4 to 14 days, preferably about 5 to 12 days. A desired SL-containing composition that provides the effects of the present invention can be prepared and obtained by treating the SL-containing culture product according to a method described later.

Treatment of SL-Containing Culture Product and Method for Recovering SL-Containing Composition The SL-containing culture products produced by the methods described above contain SL-producing yeast (fungal cells), and medium components such as unused hydrophobic substrate and hydrophilic substrate, as well as produced SL. Thus, it is preferred to remove the fungal cells and the medium components so as to prepare an SL-containing composition containing SL in a relatively high percentage. The SL-containing composition according to the present invention is preferably an SL-containing composition prepared by removing fungal cells and medium components from an SL-containing culture product. The method for removing fungal cells and medium components from an SL-containing culture product to recover the SL-containing composition according to the present invention can be a combination of known methods to the extent that the effects of the present invention are not interfered with.

Specifically, as described in Production Example 1 below, an (acidic) SL-containing culture product that has been allowed to stand at room temperature separates into the following three layers from the bottom: a brownish liquid layer mainly containing SL, a milky white solid layer mainly containing fungal cells, and a supernatant layer mainly containing foreign substances in the medium. An (acidic) SL-containing culture product that has been subjected to heat sterilization and then allowed to stand at room temperature also separates into three layers in the same manner. After the supernatant layer is removed, water in an amount equivalent to that of the supernatant layer is added, and the pH is adjusted to about 6 to 7 with an aqueous sodium hydroxide solution to solubilize SL. Subsequently, the adjusted solution is centrifuged, and, for example, an aqueous sulfuric acid solution is added to the recovered supernatant to adjust the pH to about 2 to 3, thereby insolubilizing SL. After the insolubilized SL is allowed to stand, decantation is performed, thereby obtaining an SL-containing composition in the form of a hydrous material containing about 40 to 55% of water. The details are given in Production Example 1 described later. This method is disclosed, for example, in JP2003-9896A (Patent Literature 4) as a method for recovering SL contained in an SL-containing culture product at a high yield.

The thus-prepared SL-containing composition contains SL (acidic SL, lactonic SL, and dimeric SL) in the proportions as described above without limitation and includes those composed substantially of these sophorolipids. The SL-containing composition may also contain a fatty acid in such a proportion as to give a hexane extract content of 6 mass % or lower, as well as SL. The SL-containing composition includes those consisting essentially of SL and a fatty acid. The method for calculating the content of a hexane extract is explained in detail in the Examples below.

The fatty acid is not limited as long as the fatty acid does not interfere with the sedimentation property and/or low-temperature fluidity, which are characteristics of the SL-containing composition according to the present invention. From Experimental Example 1, described below, the fatty acid includes $C_{6-8}$ or $C_{18}$ saturated fatty acids (hexanoic acid, octanoic acid, and stearic acid), and $C_{18}$ unsaturated fatty acids (oleic acid, linoleic acid, and linolenic acid).

The terms "containing" and "comprising" as used here include the meanings of consisting essentially of and consisting of.

EXAMPLES

In order to aid understanding of the structure and effects of the present invention, the present invention is described below with reference to Production Examples and Experimental Examples. However, the present invention is not limited to these Production Examples and Experimental Examples. Unless otherwise specified, the following experiments were conducted at room temperature (20±5° C.) under atmospheric pressure. Unless otherwise specified, the unit "%" means mass %, and the unit "parts" means parts by mass.

The starting materials used in the Production Examples and Experiment Examples described below and the measurement methods and evaluation methods are given below. Table 2 lists the physical properties (iodine value, melting point, freezing point) of the vegetable oils used as a starting material, the fatty acid composition (wt %) of the triglycerides (the main component of the vegetable oils), and the fatty acid composition of the fatty acids used as a starting material.

Starting Material

- Palm Olein: trade name, NBD Palm Olein IV 56 (available from Unitata Berhad) safflower oil (high linoleic): trade name, Safflower Salad Yu (available from Summit Oil Mill Co., Ltd.)
- Soybean Oil: trade name, Diazu Shirashime Yu (available from Summit Oil Mill Co., Ltd.)
- Rapeseed Oil (Shirashime oil): trade name, Natane Shirashime Yu (available from Summit Oil Mill Co., Ltd.)
- Sunflower Oil (high oleic): trade name, High Oleic Himawari Yu (available from Summit Oil Mill Co., Ltd.)
- Safflower oil (high oleic): trade name, High Oleic Safflower Yu (available from Summit Oil Mill Co., Ltd.)
- Fatty acid (HE1885): trade name, Nouracid HE 1885 (containing 21 wt % or higher of palmitic acid and 64 wt % or higher of oleic acid) (available from Oleon)
- Fatty Acid (NAA-34): trade name, NAA-34 (containing 21 wt % or higher of palmitic acid and 58 wt % or higher of oleic acid) (available from NOF Corporation)
- Glucose: trade name, Nisshoku Gansui Kesshou Budoutou [hydrous crystalline glucose] (available from Nihon Shokuhin Kako Co., Ltd.)
- Inorganic Acid Salt: $KH_2PO_3$, $MgSO_4$, NaCl (formulation (mass ratio): 10:5:1)
- Yeast Extract: trade name, Meast Powder N (available from Asahi Food & Healthcare, Ltd.)
- Peptone: trade name, Peptone from *Glycine max* (available from Sigma-Aldrich)

TABLE 3

| Vegetable Oil | Iodine Value | Melting Point, Freezing Point ° C. | Fatty Acid Composition of Triglyceride (wt %) | | | | | | | | | | | |
|---|---|---|---|---|---|---|---|---|---|---|---|---|---|---|
| | | | C12:0 | C14:0 | C16:0 | C16:1 | C18.0 | C18:1 | C18:2 | C16:3 | C20.0 | C20:1 | C22:0 | C24:0 |
| Palm Olein | 56-72 | 24≤ | 0.3 | 1 | 35.4 | 0.2 | 3.7 | 46.1 | 12.5 | 0.2 | 0.3 | — | — | — |
| Safflower Oil (High Linoleic) | 140-150 | −5 | — | — | 6.4 | — | 2.5 | 16.8 | 73 | 0.4 | 0.4 | 0.2 | 0.2 | 0.1 |
| Soybean Oil | 123-142 | −7 to −8 | — | — | 10.6 | — | 4.1 | 25.3 | 52.2 | 6.6 | 0.4 | 0.2 | 0.4 | 0.2 |
| Rapeseed Oil (Shirashime Yu) | 94-126 | 0 to −12 | 0 | 4.1 | 0.2 | 1.8 | 64 | 18.7 | 5.8 | 0.6 | 1.1 | 0.3 | 0.2 | 0.2 |
| Sunflower Oil (High Oleic) | 78-88 | <8 | — | — | 3.7 | 0.1 | 2.8 | 83.7 | 7.8 | 0.2 | 0.3 | 0.3 | 0.9 | 0.3 |
| Safflower Oil (High Oleic) | 88-95 | −5 | — | — | 4.8 | — | 2 | 78.1 | 13.7 | 0.2 | 0.4 | 0.3 | 0.3 | — |

TABLE 3-continued

| | Fatty Acid Composition (wt %) | | | | | | | | | | | |
|---|---|---|---|---|---|---|---|---|---|---|---|---|
| Fatty Acid | C12:0 | C14:0 | C14:1 | C15. | C16:0 | C16:1 | C17.1 | C18:0 | C18:1 | C16:2 | C18.3 | C20:0 |
| Fatty Acid (HE 1885) | 0.00 | 0.50 | 0.00 | 0.00 | 21.66 | 0.00 | 0.00 | 3.78 | 64.48 | 9.07 | 0.05 | 0.81 |
| Fatty Acid (NAA-34) | 0.05 | 1.35 | 0.65 | 0.10 | 21.65 | 3.60 | 0.70 | 2.90 | 58.50 | 9.20 | 0.80 | 0.00 |

Measurement Method (1) Method for Calculating SL Content in SL-Containing Composition and SL Composition An SL-containing composition is diluted with ethanol (99.5 v %) to give a dry residue of about 1%, and the prepared ethanol-diluted product is subjected to high-performance liquid chromatography (HPLC) under the conditions shown in Table 1. The method for measuring the dry residue is described in section (2) later.

In HPLC under the conditions shown in Table 1, monomeric acidic SL elutes in the regions at a retention time of 10 to 23 minutes (acidic SLa) and 45 to 58 minutes (acidic SLb). Monomeric lactonic SL (which contains diacetyl lactonic SL; the same applies below) elutes in the region at a retention time of 23 to 40 minutes. Of the peaks that appear in this region, particularly in the region of 28 to 33 minutes, the peak with the highest intensity is derived from oleic acid-diacetyl lactonic SL. Dimeric SL elutes in the region at a retention time of 58 to 70 minutes.

The amount of acidic SL, lactonic SL, and dimeric SL contained in the SL-containing composition is calculated by using a calibration curve prepared from each peak area obtained from the HPLC analysis with a standard sample of known concentration. The total SL amount in the SL-containing composition is determined by adding up each content of acidic SLa, acidic SLb, lactonic SL, and dimeric SL. The proportion (SL composition %) of each SL (acidic SL, lactonic SL, dimeric SL) in the total amount of SL (100 mass %) contained in the SL-containing composition can be calculated from the peak area ratio in the HPLC analysis. The proportion of oleic acid-diacetyl lactonic SL in the total amount of lactonic SL (100 mass %) can also be calculated from the peak area ratio in the HPLC analysis.

(2) Method for Measuring Dry Residue and Water Content in SL-Containing Composition 1. A petri dish is paved with dry glass beads (bead diameter: 3.0 mm) and covered with a lid, followed by precisely measuring the entire weight (container weight).
2. A mixed and homogenized SL-containing composition (hydrous material) is spread over the entire top of the beads in the petri dish, which is then covered promptly and weighed (weight before drying) precisely.
3. The petri dish is transferred to a dryer (constant-temperature dryer DY300: Yamato Scientific Co., Ltd.) at 105° C. and dried for 3 hours without the lid.
4. The petri dish is covered with the lid and transferred to a desiccator containing a drying agent (silica gel), cooled to room temperature, and weighed (weight after drying) precisely.
5. The dry residue and water content are calculated from the following formula.

$$\text{Dry Residue (wt \%)}=(A/B)\times 100$$

$$\text{Water Content (wt \%)}=100-\text{Dry Residue (wt \%)}$$

A: Weight of SL-containing Composition after Drying (g) (=Weight after Drying (g)−Weight of Container (g))

B: Weight of SL-containing Composition before Drying (g) (=Weight before Drying (g)−Weight of Container (g))

(3) Method for Measuring Hexane Extract Content in SL-Containing Composition

1. The weight of a centrifuge tube and a beaker is precisely measured beforehand.
2. About 5 g of a mixed and homogenized SL-containing composition are placed in the centrifuge tube, and the weight (weight a) is precisely measured.
3. n-Hexane in an amount equivalent to that of the taken SL-containing composition is added, and the tube is tightly sealed, followed by mixing with intensive shaking.
4. Centrifugation is performed at 1000×g for 10 minutes.
5. Only the hexane layer is taken with a pipette or similar device and placed in the beaker.
6. The above extract extraction operation is performed three times. This operation is performed after the temperature of the SL-containing composition and n-hexane is adjusted to room temperature (20±5° C.).
7. The beaker containing the recovered hexane layer is heated in a hot-water bath (about 80° C.) to volatilize the hexane, and then the weight (weight b) is precisely measured.
8. The hexane extract content (on a wet-weight basis and on a dry-weight basis) is calculated from the following formula.

$$\text{Hexane Extract Content (wt \%, on a wet-weight basis)}=(A/B)\times 100$$

A: Weight of Residue in Beaker (g) (=Weight b (g)−Weight of Beaker (g))

B: Weight of SL-containing Composition (g) (=Weight a (g)−Weight of Centrifuge Tube (g))

$$\text{Hexane Extract Content (wt \%, on a dry weight basis)}=(\text{Hexane Extract Content (wt \%, on a wet-weight basis)}/\text{Dry Residue (wt \%)})\times 100$$

(4) Method for Setting Amount of Oxygen Supplied to Culture Product During Culture Period Oxygen mass transfer coefficient ($k_La$) was used as the index for the amount of oxygen supplied to a culture product during the culture period.

Specifically, 3 L of tap water (pseudo-culture) is placed in a 5 L-culture tank for use in actual culture (without inoculation of fungi), and the oxygen mass transfer coefficient ($k_La$) in culture (pseudo-culture) under the culture conditions (30° C.) to be actually applied is measured according to a sodium sulfite method with an exhaust gas analyzer (measurement gas: $O_2$).

The thus-measured oxygen mass transfer coefficient ($k_La$) is referred to as "apparent oxygen mass transfer coefficient ($k_La$)" below.

1. An exhaust gas analyzer (OFF-GAS Jr. DEX-2561-1: ABLE Corporation) is calibrated to the oxygen label in air.
2. Sodium sulfite is dissolved in tap water to prepare 3 L of an aqueous sodium sulfite solution (concentration: 0.4 mol/

L). 3 mL of an aqueous copper sulfate solution (concentration: 0.1 mol/L) is added to the prepared aqueous sodium sulfite solution.

3. Incubation is conducted at 30° C. under the culture conditions to be actually applied (e.g., aeration volume, agitation (rotation speed)), and $k_La$ is calculated from the dissolved oxygen level in the culture tank (in water), the saturated dissolved oxygen level in water, the oxygen level in air, the aeration volume, and the oxygen level in exhaust gas.

Specifically, the apparent oxygen mass transfer coefficient ($k_La$) was determined based on formula 2 calculated from the following formula 1.

$$dC/dt=k_La(C^*-C)-R \quad \text{(formula 1)}$$

C: Dissolved oxygen level in culture tank (in water) (mg/L) (The value measured 20 minutes after the aeration volume and agitation (rotation speed) are set is used. However, because sodium sulfite is added to tap water here, C=0.)

C*: Saturated dissolved oxygen level in water (A saturated dissolved oxygen level in water at 30° C. (7.53 mg/L) is used.)

$k_La$: Oxygen mass transfer coefficient

R: Respiration rate (mg·$O_2$/L/h)

(Because measurement is performed in the absence of fungal cells, R=0)

$$k_La=dC/dt/7.53 \quad \text{(formula 2)}$$

dC/dt: Change in dissolved oxygen level in culture tank (in water) per unit time during pseudo-culture (Oxygen Consumption (mg/L/h) in culture tank (in water))

Physical Properties Evaluation Method (1) Evaluation of Viscosity (mPa·s)

1. 55 g of an SL-containing composition is placed in a PET container (standard bottle (No. 5): 50-mL volume, inner diameter 24.7 mm, body diameter 38 mm, body height 68.5 mm), and allowed to stand in the dark at −5° C. for 72 hours.

2. After the SL-containing composition is allowed to stand, the viscosity of the SL-containing composition at a product temperature of −5° C. is measured with the following instrument under the following conditions.

Measurement Instrument: TVB-10M viscometer (Toki Sangyo Co., Ltd) Rotor and Agitation Rotation Speed: see Table 2 Measurement Time: 1 minute (2) Evaluation of Sedimentation Property (2-1) Sedimentation Property of SL-Containing Composition in SL-Containing Culture Product 1. An SL-containing culture product after completion of culture is placed in a centrifuge tube.

2. The culture product is adjusted to a product temperature of 20° C., and the centrifuge tube is shaken well by hand for 10 seconds to agitate the sample.

3. The agitated culture product in the centrifuge tube is allowed stand as is at 20° C. in the dark for 12 hours.

4. After being allowed to stand, the culture product is visually observed for whether sediment is present in the centrifuge tube, and evaluated according to the following criteria.

○ Having a sedimentation property: Sediment is observed.

x No sedimentation property: No sediment is observed.

(2-2) Sedimentation Property of SL-Containing Composition in Distilled Water (Confirmation of Whether Separation and Sediment are Present)

1. 5 g of an SL-containing composition adjusted to give a dry residue of 50%, and 25 g of distilled water are added to a centrifuge tube.

2. The pH of the sample (water content: 91.7%) is adjusted to 2.5 to 3.0 with hydrochloric acid, sulfuric acid, sodium hydroxide, potassium hydroxide, etc. with a pH meter (HM-30G, DKK-TOA Corporation).

3. With the sample adjusted to a product temperature of 20° C., the centrifuge tube is shaken well by hand for 10 seconds to agitate the sample, and then allowed to stand at 20° C. for 5 minutes.

4. After being allowed to stand, the sample is visually observed for whether sediment is present in the centrifuge tube, and evaluated according to the following criteria.

○ Having a sedimentation property: Obvious separation and/or sediment (a transparent supernatant (aqueous layer) and a milky or brownish sediment layer (SL-containing composition)) are observed.

x No sedimentation property: The entire centrifuge tube is uniformly clear or slightly opaque, with no separation or sediment observed.

(3) Evaluation of Low-Temperature Fluidity 1. 15 g of an SL-containing composition is placed in a PET container (standard bottle (No. 5)), covered with a lid, and allowed to stand at −5° C. in the dark for 3 days (72 h). When the water content of the SL-containing composition is not 50%, an SL-containing composition having its water content adjusted to 50% is used.

2. After being allowed to stand, the container is inverted upside-down at −5° C. The fluidity of the contents is visually observed for 30 seconds, and evaluated according to the following criteria.

○ Excellent low-temperature fluidity: the contents have fluidity. The contents present at the bottom of the container before inversion flow toward the mouth of the container within 30 seconds after the container is inverted.

Δ Having low-temperature fluidity: Although the contents have fluidity, it takes more than 30 seconds for the contents that are on the bottom of the container before inversion to move to the mouth of the container after inversion.

x Poor low-temperature fluidity: The contents have no fluidity at all. The contents that are on the bottom of the container do not flow at all or remain solid and fall to the mouth of the container.

Production Example 1: Production of SL-Containing Composition (Production Method 1)

(1) Pre-Culture

The culture medium for use was a liquid medium containing 10 g of glucose, 10 g of peptone, and 5 g of a yeast extract per litter of water. An SL-producing yeast (*Starmerella bombicola* ATCC22214 strain) was subjected to shake culture at 30° C. for 2 days, and this was determined to be a pre-culture broth.

(2) Main Culture 120 mL of the pre-culture broth was inoculated into a main culture medium (3 L) placed in a 5-L fermenter (desktop fermenter, Bioneer-NEO: B. E. Marubishi Co., Ltd.), and subjected to aerated agitation culture at 30° C. for 5 days to ferment the broth. The conditions for aerated agitation culture were set such that the amount of oxygen supplied to the medium in terms of apparent oxygen mass transfer coefficient ($k_La$) was 540 l/hr (aeration volume: 1.8 L/min, stirring speed: 600 rpm).

The main culture medium for use was prepared by adding the hydrophobic substrate (vegetable oil, fatty acid) and the hydrophilic substrate (glucose, a yeast extract, and urea)

shown in Table 3 to water to form an aqueous liquid medium containing an inorganic salt (pH before sterilization: 4.5 to 4.8). During the culture period, the pH of the culture product was not controlled.

On the 6th day from the start of culture, the culture was ended. The culture product (pH: about 3) removed from the fermenter was heated to 50 to 80° C., then returned to room temperature (25° C.), and allowed to stand for 1 or more days. As a result, the culture product was separated into the following three layers in the order from the bottom: a brown liquid layer; a milky-white solid layer presumably mainly containing fungal cells; and a supernatant. After the supernatant was removed, industrial water or groundwater was added in an amount equal to the amount of the supernatant removed. While the resulting mixture was stirred, a 48% aqueous sodium hydroxide solution was gradually added to adjust the pH to 6.5 to 6.9, thus solubilizing SL contained in the culture product. The resulting product was centrifuged by a tabletop centrifuge (Westfalia: Westfalia Separator AG; 2,400×g, 15 minutes, room temperature (25° C.)) to precipitate milky-white solids (fungal cells), and a supernatant containing SL was collected. While the collected supernatant was stirred, an aqueous sulfuric acid solution with a concentration of 62.5% was gradually added to adjust the pH to 2.5 to 3.0, thus insolubilizing SL. After the resulting mixture was allowed to stand for 2 days at room temperature (25° C.), the supernatant was removed by decantation as much as possible, thus obtaining the residue (hydrous material) as an SL-containing composition.

The thus-obtained SL-containing composition was measured for the total SL amount, the SL composition (%), the proportion of the oleic acid-diacetyl lactonic SL contained in the lactonic SL (%), the water content, and the hexane extract content according to the methods described above. The total SL amount, the SL composition, and the proportion of oleic acid-diacetyl lactonic SL were determined from the peak area of each region obtained by diluting the obtained SL-containing composition with ethanol (99.5 v %) to give a dry residue of about 1%, and then subjecting the diluted product to HPLC under the conditions described above.

The thus-obtained SL-containing composition was evaluated for viscosity (mPa·s), sedimentation property, and low-temperature fluidity according to the methods described above. Table 4-1 (Examples 1-1 to 1-14) and Table 4-2 (Comparative Examples 1-1 to 1-7) show the results collectively. Tables 4-1 and 4-2 show the measurement and evaluation results of the SL-containing compositions obtained by culture without pH control of the culture products during the culture period (the initial pH of about 5 decreased to 3 over the course of culture), with the conditions for aerated agitation culture being set such that the amount of oxygen supplied to each culture product in terms of apparent oxygen mass transfer coefficient ($k_La$) was the value (l/hr) shown in the tables.

Table 4-2 also shows the results of measuring and evaluating existing SL-containing compositions (commercial products 1 to 5) for the total SL amount, the SL composition (%), the proportion of oleic acid-diacetyl lactonic SL (%) contained in lactonic SL, the water content, the hexane extract content, the viscosity, the sedimentation property, and the low-temperature fluidity in the same manner as above.

TABLE 4-1

| | | | | Example 1-1 | Example 1-2 | Example 1-3 | Example 1-4 | Example 1-5 |
|---|---|---|---|---|---|---|---|---|
| Medium & Culture Conditions | Hydrophobic Substrate | Vegetable Oil | Palm Olein | 8 | 7 | 5 | 5 | — |
| | | | Safflower Oil | — | — | — | — | — |
| | | | Soybean Oil | — | — | — | — | — |
| | | | Rapeseed Oil (*Shirashime Yu*) | — | — | — | — | — |
| | | | High Oleic Safflower Oil | — | — | — | — | — |
| | | | High Oleic Sunflower Oil | — | — | — | — | — |
| | | Fatty Acid | Fatty Acid (NAA-34) | 2 | 3 | 5 | 5 | 10 |
| | | Total Amount of Free Fatty Acid | | 2 | 3 | 5 | 5 | 10 |
| | Hydrophilic Substrate | Glucose | | 10 | 10 | 10 | 10 | 10 |
| | | Urea | | 0.1 | 0.1 | 0.1 | 0.1 | 0.1 |
| | | Yeast Extract | | 0.25 | 0.25 | 0.25 | 0.25 | 0.25 |
| | Others | Inorganic Salt | | 1.6 | 1.6 | 1.6 | — | 1.6 |
| | Distilled Water | | | Remainder | Remainder | Remainder | Remainder | Remainder |
| | Total Amount (wt %) | | | 100 | 100 | 100 | 100 | 100 |
| | pH Control during Culture | | | Not Controlled | Not Controlled | Not Controlled | Not Controlled | Not Controlled |
| | Aerated Agitation Conditions (Amount of Oxygen Supplied to Culture Product) (Apparent $K_La$ (1/hr)) | | | 540 | 540 | 540 | 540 | 540 |
| SL-containing Composition | SL Composition (%) | Acidc SL | | 17.2 | 24.8 | 18.3 | 36.4 | 32.3 |
| | | Lactonic SL | | 45.9 | 54.2 | 53.7 | 50.0 | 67.2 |
| | | Dimeric SL | | 36.9 | 21.0 | 28.0 | 13.6 | 0.5 |
| | Proportion of Oleic Acid-dacetyl Lactonic SL in Lactonic SL (100%) | | | 77.2 | 83.3 | 91.8 | 89.1 | 90.1 |
| | Water Content (100 − Dry Residue) (%) | | | 50.2 | 43.8 | 44.1 | 51.6 | 45.0 |
| | Hexane Extract: Wet-Weight Basis (%) (Dry-Weight Basis (%)) | | | 1.05 (2.11) | 0.044 (0.078) | 0.20 (0.36) | 0.054 (0.11) | 0.66 (1.20) |

TABLE 4-1-continued

| | | | | | | | | |
|---|---|---|---|---|---|---|---|---|
| Physical Properties Evaluation | Viscosity (mPa · s) | | | ND | 2310.0 | 2990.0 | ND | 4100.0 |
| | Sedimentation Property | Sedimentation Property in Culture Product | | ○ | ○ | ○ | ○ | ○ |
| | | Sedimentation Property in Distilled Water | | ○ | ○ | ○ | ○ | ○ |
| | Low-temperature Fluidity | | | ○ | ○ | ○ | ○ | ○ |
| | Result | | | ○ | ○ | ○ | ○ | ○ |

| | | | | Example 1-6 | Example 1-7 | Example 1-8 | Example 1-9 | Example 1-10 |
|---|---|---|---|---|---|---|---|---|
| Medium & Culture Conditions | Hydrophobic Substrate | Vegetable Oil | Palm Olein | — | 5 | 7 | 7 | 7 |
| | | | Safflower Oil | — | — | — | — | — |
| | | | Soybean Oil | — | — | — | — | — |
| | | | Rapeseed Oil (*Shirashime Yu*) | — | — | — | — | — |
| | | | High Oleic Safflower Oil | — | — | — | — | — |
| | | | High Oleic Sunflower Oil | — | — | — | — | — |
| | | Fatty Acid | Fatty Acid (NAA-34) | 10 | 5 | 3 | 3 | 3 |
| | | Total Amount of Free Fatty Acid | | 10 | 5 | 3 | 3 | 3 |
| | Hydrophilic Substrate | Glucose | | 10 | 10 | 10 | 10 | 10 |
| | | Urea | | 0.1 | 0.1 | 0.1 | 0.1 | 0.1 |
| | | Yeast Extract | | 0.25 | 0.25 | 0.25 | 0.25 | 0.25 |
| | Others | Inorganic Salt | | — | 1.6 | 1.6 | 1.6 | 1.6 |
| | Distilled Water | | | Remainder | Remainder | Remainder | Remainder | Remainder |
| | Total Amount (wt %) | | | 100 | 100 | 100 | 100 | 100 |
| | pH Control during Culture | | | Not Controlled | Not Controlled | Not Controlled | Not Controlled | Not Controlled |
| | Aerated Agitation Conditions (Amount of Oxygen Supplied to Culture Product) (Apparent $K_La$ (1/hr)) | | | 540 | 200 | 200 | 300 | 400 |
| SL-containing Composition | SL Composition (%) | Acidc SL | | 45.2 | 23.6 | 19.4 | 32.6 | 26.0 |
| | | Lactonic SL | | 46.4 | 47.8 | 49.5 | 47.3 | 58.0 |
| | | Dimeric SL | | 8.4 | 28.6 | 31.1 | 20.1 | 16.0 |
| | Proportion of Oleic Acid-dacetyl Lactonic SL in Lactonic SL (100%) | | | 82.1 | 86.1 | 75.9 | 77.6 | 77.5 |
| | Water Content (100 − Dry Residue) (%) | | | 44.6 | 44.4 | 42.9 | 35.6 | 44.2 |
| | Hexane Extract: Wet-Weight Basis (%) (Dry-Weight Basis (%)) | | | 0.33 (0.59) | 0.87 (1.57) | 0.21 (0.36) | 0.42 (0.66) | 0.25 (0.45) |
| Physical Properties Evaluation | Viscosity (mPa · s) | | | 7200.0 | 9930.0 | 7300 | 18980 | 9690 |
| | Sedimentation Property | Sedimentation Property in Culture Product | | ○ | ○ | ○ | ○ | ○ |
| | | Sedimentation Property in Distilled Water | | ○ | ○ | ○ | ○ | ○ |
| | Low-temperature Fluidity | | | ○ | ○ | ○ | ○ | ○ |
| | Result | | | ○ | ○ | ○ | ○ | ○ |

| | | | | Example 1-11 | Example 1-12 | Example 1-13 | Example 1-14 |
|---|---|---|---|---|---|---|---|
| Medium & Culture Conditions | Hydrophobic Substrate | Vegetable Oil | Palm Olein | 8 | 2.5 | 0 | 0 |
| | | | Safflower Oil | — | — | — | — |
| | | | Soybean Oil | — | — | — | — |
| | | | Rapeseed Oil (*Shirashime Yu*) | — | — | — | — |
| | | | High Oleic Safflower Oil | — | — | — | — |
| | | | High Oleic Sunflower Oil | — | — | — | — |
| | | Fatty Acid | Fatty Acid (NAA-34) | 2 | 7.5 | 10 | 10 |
| | | Total Amount of Free Fatty Acid | | 2 | 7.5 | 10 | 10 |
| | Hydrophilic Substrate | Glucose | | 10 | 10 | 10 | 10 |
| | | Urea | | 0.1 | 0.1 | 0.1 | 0.1 |
| | | Yeast Extract | | 0.25 | 0.25 | 0.25 | 0.25 |
| | Others | Inorganic Salt | | 1.6 | 1.6 | 1.6 | 1.6 |
| | Distilled Water | | | Remainder | Remainder | Remainder | Remainder |
| | Total Amount (wt %) | | | 100 | 100 | 100 | 100 |
| | pH Control during Culture | | | Not Controlled | Not Controlled | Not Controlled | Not Controlled |
| | Aerated Agitation Conditions (Amount of Oxygen Supplied to Culture Product) (Apparent $K_La$ (1/hr)) | | | 200 | 200 | 200 | 300 |

TABLE 4-1-continued

| | | | | | | |
|---|---|---|---|---|---|---|
| SL-containing Composition | SL Composition (%) | Acidc SL | 27.2 | 39.3 | 33.3 | 36.4 |
| | | Lactonic SL | 46.7 | 54.1 | 65.6 | 61.5 |
| | | Dimeric SL | 26.1 | 6.5 | 1.1 | 2.2 |
| | Proportion of Oleic Acid-dacetyl Lactonic SL in Lactonic SL (100%) | | 68.3 | 86.2 | 87.6 | 88.2 |
| | Water Content (100 − Dry Residue) (%) | | 50.3 | 36.8 | 38.0 | 37.3 |
| | Hexane Extract: Wet-Weight Basis (%) (Dry-Weight Basis (%)) | | 0.12 (0.24) | 0.40 (0.63) | 0.54 (0.87) | 0.8 (1.28) |
| Physical Properties Evaluation | Viscosity (mPa · s) | | 4080 | 5000 | 5100 | 5200 |
| | Sedimentation Property | Sedimentation Property in Culture Product | ○ | ○ | ○ | ○ |
| | | Sedimentation Property in Distilled Water | ○ | ○ | ○ | ○ |
| | Low-temperature Fluidity | | ○ | ○ | ○ | ○ |
| | Result | | ○ | ○ | ○ | ○ |

TABLE 4-2

| | | | | Comparative Example 1-1 | Comparative Example 1-2 | Comparative Example 1-3 | Comparative Example 1-4 | Comparative Example 1-5 | Comparative Example 1-6 |
|---|---|---|---|---|---|---|---|---|---|
| Medium & Culture Conditions | Hydrophobic Substrate | Vegetable Oil | Palm Olein | 9 | 10 | — | — | — | — |
| | | | Safflower Oil | — | — | 10 | — | — | — |
| | | | Soybean Oil | — | — | — | 10 | — | — |
| | | | Rapeseed Oil (*Shirashime Yu*) | — | — | — | | 10 | — |
| | | | High Oleic Safflower Oil | — | — | — | — | — | 10 |
| | | | High Oleic Sunflower Oil | —— | — | — | — | — | — |
| | | Fatty Acid | Fatty Acid (NAA-34) | 1 | — | — | — | — | — |
| | | Total Amount of Free Fatty | | 1 | 0 | 0 | 0 | 0 | 0 |
| | Hydrophilic Substrate | Glucose | | 10 | 10 | 10 | 10 | 10 | 10 |
| | | Urea | | 0.1 | 0. | 0.1 | 0.1 | 0.1 | 0.1 |
| | | Yeast Extract | | 0.25 | 0.25 | 0.25 | 0.25 | 0.25 | 0.25 |
| | Others | Inorganic Salt | | 1.6 | 1.6 | 1.6 | 1.6 | — | 1.6 |
| | Distilled Water | | | Remainder | Remainder | Remainder | Remainder | Remainder | Remainder |
| | Total Amount (wt %) | | | 100 | 100 | 100 | 100 | 100 | 100 |
| | pH Control during Culture | | | Not Controlled | Not Controlled | Not Controlled | Not Controlled | Not Controlled | Not Controlled |
| | Aerated Agitation Conditions (Amount of Oxygen Supplied to Culture Product) (Apparent $K_La$ (1/hr)) | | | 540 | 540 | 540 | 540 | 540 | 540 |
| SL-containing Composition | SL Composition (%) | Acidic SL | | 16.5 | 14.1 | 77.1 | 77.7 | 38.9 | 26.8 |
| | | Lactonic SL | | 15.5 | 18.3 | 11.5 | 14.1 | 30.5 | 25 |
| | | Dimeric SL | | 68 | 67.6 | 11.4 | 8.2 | 30.5 | 48.2 |
| | Proportion of Oleic Acid-diacetyl Lactonic SL in Lactonic SL (100%) | | | 72.1 | 63 | 30 | 51 2 | 88.3 | 92 |
| | Water Content (100 − Dry Residue) (%) | | | 49.4 | 57.5 | 61.8 | 62.1 | 51.2 | 47.8 |
| | Hexane Extract: Wet-Weight Basis (%) (Dry-Weight Basis (%)) | | | 0 (0) | 0.050 (0.117) | 0.21 (0.56) | 0.023 (0.061) | 0.88 (1.81) | 0.29 (0.55) |
| Physical Properties Evaluation | Viscosity (mPa · s) | | | 522 | 130.7 | 54.5 | 99 9 | 476.3 | 871 |
| | Sedimentation Property | Sedimentation Property in Culture Product | | x | x | x | x | x | x |
| | | Sedimentation Property in Distilled Water | | x | x | x | x | x | x |
| | Low-temperature Fluidity | | | ○ | ○ | ○ | ○ | ○ | ○ |
| | Result | | | x | x | x | x | x | x |

| | | | | Comparative Example 1-7 | Commercial Product 1 | Commercial Product 2 | Commercial Product 3 | Commercial Product 4 | Commercial Product 5 |
|---|---|---|---|---|---|---|---|---|---|
| Medium & Culture Conditions | Hydrophobic Substrate | Vegetable Oil | Palm Olein | — | | | | | |
| | | | Safflower Oil | — | | | | | |
| | | | Soybean Oil | — | | | | | |
| | | | Rapeseed Oil (*Shirashime Yu*) | — | | | | | |
| | | | High Oleic Safflower Oil | — | | | | | |
| | | | High Oleic Sunflower Oil | 10 | | | | | |
| | | Fatty Acid | Fatty Acid (NAA-34) | 1 | | | | | |
| | | Total Amount of Free Fatty | | 0 | | | | | |

TABLE 4-2-continued

| | | | | | | | | |
|---|---|---|---|---|---|---|---|---|
| | Hydrophilic Substrate | Glucose | 10 | | | | | |
| | | Urea | 0.1 | | | | | |
| | | Yeast Extract | 0.25 | | | | | |
| | Others | Inorganic Salt | 1.6 | | | | | |
| | Distilled Water | | Remainder | | | | | |
| | Total Amount (wt %) | | 100 | | | | | |
| | pH Control during Culture | | Not Controlled | | | | | |
| | Aerated Agitation Conditions (Amount of Oxygen Supplied to Culture Product) (Apparent $K_La$ (1/hr)) | | 540 | | | | | |
| SL-containing Composition | SL Composition (%) | Acidic SL | 17.3 | 13.1 | 35.7 | 13.2 | 27.8 | 6.2 |
| | | Lactonic SL | 26.2 | 44.7 | 64.3 | 86.6 | 39.8 | 93.8 |
| | | Dimeric SL | 56.6 | 42.3 | 0 | 0.2 | 32.4 | 0 |
| | Proportion of Oleic Acid-diacetyl Lactonic SL in Lactonic SL (100%) | | 96 | 82.9 | 95.6 | 74 | 13.6 | 83.5 |
| | Water Content (100 − Dry Residue) (%) | | 53.1 | 50.6 | 39.8 | 37 | 66.2 | 36.4 |
| | Hexane Extract: Wet-Weight Basis (%) (Dry-Weight Basis (%)) | | 0.16 (0.34) | 0 (0) | 0 (0) | — | 0.36 (1.07) | 0.97 (1.53) |
| Physical Properties Evaluation | Viscosity (mPa · s) | | ND | 338.5 | ND | ND | ND | ND |
| | Sedimentation Property | Sedimentation Property in Culture Product | x | x | ○ | x | x | ○ |
| | | Sedimentation Property in Distilled Water | x | x | ○ | ○ | x | ○ |
| | Low-temperature Fluidity | | ○ | ○ | x | x | ○ | x |
| | Result | | x | x | x | x | x | x |

As shown in Table 4-2, under these culture conditions, when the hydrophobic substrate added to the medium was only a vegetable oil, the prepared SL-containing compositions were not confirmed to have a sedimentation property (see Comparative Examples 1-2 to 1-7). Additionally, when the hydrophobic substrate was a vegetable oil and a fatty acid with the proportion of the free fatty acid being 10% or lower of the total amount (100%), the SL-containing composition was also not confirmed to have a sedimentation property as in the case above (see Comparative Example 1-1). This suggests that the SL generated in these cases were solubilized in the culture product.

However, as shown in Table 4-1, when the hydrophobic substrate added to the medium was a vegetable oil and a fatty acid with the proportion of the free fatty acid being 20% or higher of the total amount (100%), the prepared SL-containing compositions were confirmed to have a sedimentation property (Examples 1-1 to 1-4, and 1-7 to 1-14). This suggests that the SL generated in these cases were insolubilized in the culture product. Additionally, when the hydrophobic substrate added to the medium was only a fatty acid, the prepared SL-containing compositions were also confirmed to have a sedimentation property (insolubilization of SL, see Examples 1-5 and 1-6). These SL-containing compositions (Examples 1-1 to 1-14) were also all excellent in fluidity at −5° C. (low-temperature fluidity).

These results revealed that when the hydrophobic substrate is only a fatty acid or when the hydrophobic substrate is a vegetable oil with a melting point of 30° C. or lower and a fatty acid with the proportion of the free fatty acid being 20 to 100% of the total amount (100%), an SL-containing composition (Examples 1-1 to 1-14) excellent in handleability in terms of both the sedimentation property and low-temperature fluidity can be prepared by setting the apparent oxygen mass transfer coefficient ($k_La$) of the culture product to preferably 200l/hr or higher without pH control during the culture period. The same results were also obtained by using fatty acid HE1885 instead of fatty acid NAA-34.

A comparison between these SL-containing compositions in terms of composition and physical properties revealed that an SL-containing composition can be excellent in the sedimentation property and low-temperature fluidity when the content of lactonic SL is 45 to 81%, preferably 45 to 70% of the total SL amount taken as 100%; the content of oleic acid-diacetyl lactonic SL is 95% or lower, preferably 92% or lower of the total amount of lactonic SL taken as 100%; the hexane extract content is 6% or lower, preferably 3% or lower on a dry-weight basis (3% or lower, preferably 1.5% or lower on a wet-weight basis); the acidic SL content is 10 to 50%, preferably 15 to 50% of the total SL amount taken as 100%; and the dimeric SL content is 45% or lower, preferably 40% or lower of the total SL amount taken as 100%. Such SL-containing compositions (water content: 40 to 55%) also had fluidity at −5° C., and the viscosity was 2310 to 18980 mPa·s.

Production Example 2: Production of SL-Containing Composition (Production Method 2)

(2-1)

120 mL of a pre-culture broth prepared in the same manner as in Production Example 1 was inoculated into a main culture medium (3 L) in the same manner as in Production Example 1, and subjected to aerated agitation culture at 30° C. for 5 days to ferment the broth. The main culture medium for use was prepared by adding the hydrophobic substrate (vegetable oil, fatty acid) and the hydrophilic substrate (glucose, a yeast extract, urea) shown in Table 5 to water to form an aqueous liquid medium containing an inorganic salt (pH before sterilization: 4.5 to 4.8). During the culture period, the pH of the culture product was controlled so as to fall within the range of 4 to 5.5. The conditions for aerated agitation culture were set such that the amount of oxygen supplied to the culture product in terms of apparent oxygen mass transfer coefficient ($k_La$) was 540l/hr (aeration volume: 1.8 L/min, stirring speed: 600 rpm).

On the 6th day from the start of culture, the culture was ended, and an SL-containing composition was recovered and obtained in the same manner as in Production Example 1. The obtained SL-containing composition was measured for the total SL amount, the SL composition (%), the proportion of oleic acid-diacetyl lactonic SL contained in lactonic SL (%), the water content, and the hexane extract content according to the methods described above in the same manner as in Production Example 1. The obtained SL-containing composition was also evaluated for viscosity (mPa·s), sedimentation property, and low-temperature fluidity according to the methods described above.

Table 5 shows the results collectively.

TABLE 5

| | | | Example 2-1 | Example 2-2 | Comparative Example 2-1 | Comparative Example 2-2 | Comparative Example 2-3 | Comparative Example 2-4 |
|---|---|---|---|---|---|---|---|---|
| Medium & Culture Conditions | Hydrophobic Substrate | Vegetable Oil Palm Olein | 10 | 10 | 10 | 10 | 10 | — |
| | | Fatty Acid Fatty Acid (NAA-34) | — | — | — | — | — | 10 |
| | Hydrophilic Substrate | Glucose | 10 | 10 | 10 | 10 | 10 | 10 |
| | | Urea | 0.1 | 0.1 | 0.1 | 0.1 | 0.1 | 0.1 |
| | | Yeast Extract | 0.25 | 0.25 | 0.25 | 0.25 | 0.25 | 0.25 |
| | Others | inorganic Salt | 1.6 | 1.6 | 1.6 | 1.6 | 1.6 | 1.6 |
| | pH Control during Culture | | Controlled (pH 4.5) | Controlled (pH 5) | Controlled (pH 4) | Controlled (pH 5.5) | Not Controlled | Controlled (pH 5) |
| | Aerated Agitation Conditions (Amount of Oxygen Supplied to Culture Product) (Apparent $K_La$ (1/hr)) | | 540 | 540 | 540 | 540 | 540 | 540 |
| SL-containing Composition | SL Composition (%) | Acidic SL | 20.5 | 17.2 | 33.2 | 15.1 | 14.1 | 13 |
| | | Lactonic SL | 58.0 | 77.4 | 39.4 | 81.9 | 18.3 | 87 |
| | | Dimeric SL | 21.5 | 5.4 | 27.4 | 3 | 67.6 | 0 |
| | Proportion of Oleic Acid-diacetyl Lactonic SL in ) Lactonic SL (100% | | 58.7 | 64.6 | 55.8 | 63.2 | 63 | 86.4 |
| | Water Content (100 - Dry Residue) (%) | | 44.4 | 40.6 | 47.6 | 41.2 | 57.5 | 35.1 |
| | Hexane Extract: Wet-Weight Basis (%) (Dry-Weight Basis (%)) | | 0.17 (0.31) | 0.0033 (0.0056) | 0.20 (0.39) | 0 (0) | 0.050 (0.12) | 0.39 (0.61) |
| Physical Properties Evaluation | Viscosity (mPa • s) | | 8180.0 | 20020.0 | 1431 | ND | 130.7 | ND |
| | Sedimentation Property | Sedimentation Property in Culture Product | ○ | ○ | x | ○ | x | ○ |
| | | Sedimentation Property in Distilled Water | ○ | ○ | x | ○ | x | ○ |
| | Low-temperature Fluidity | | ○ | ○ | ○ | x | ○ | x |
| | Result | | ○ | ○ | x | x | x | x |

ND: Not Measured

As shown in Comparative Examples 1-2 to 1-7 (Table 4-2) of Production Example 1 above, when only a vegetable oil is used as a hydrophobic substrate in the medium, the prepared SL-containing composition does not have a sedimentation property unless the pH of the culture product is controlled during the culture period. As shown in Table 5, the same phenomenon was observed in Comparative Example 2-3. In contrast, the use of a vegetable oil alone as a hydrophobic substrate was confirmed to be able to provide an SL-containing composition with a sedimentation property if the pH of the culture product is controlled so as to fall within the range of 4.5 to 5 during the culture period (Examples 2-1 and 2-2). However, even under these pH control conditions, if the pH was 4 or lower, the prepared SL-containing composition did not have a sedimentation property (Comparative Example 2-1). Even under these pH control conditions, if the pH was 5.5 or higher, the prepared SL-containing composition was confirmed to have decreased low-temperature fluidity (Comparative Example 2-2).

As shown in Examples 1-5 and 1-6 (Table 4-1) of Production Example 1 above, when only a fatty acid was used as a hydrophobic substrate in the medium, the SL-containing composition prepared without pH control of the culture product during the culture period was excellent in both the sedimentation property and low-temperature fluidity; however, when the pH of the culture product was controlled to 5 during the culture period, the obtained SL-containing composition was confirmed to exhibit decreased low-temperature fluidity (Comparative Example 2-4).

Production Example 3: Production of SL-Containing Composition (Production Method 2) (2-2)

An SL-containing composition was prepared in the same manner as in Example 2-2 described in Production Example 2, except that the conditions for aerated agitation culture were set such that the amount of oxygen supplied to the culture product in terms of apparent oxygen mass transfer coefficient ($k_La$) was 160 to 367 1/hr, and that the period of the culture was 6 to 12 days. The SL-containing composition was evaluated for composition, viscosity (mPa·s), sedimentation property, and low-temperature fluidity.

Table 6 shows the results.

TABLE 6

| | | | | Example 3-1 | Example 3-2 | Comparative Example 3-1 |
|---|---|---|---|---|---|---|
| Medium & Culture Conditions | Hydrophobic Substrate | Vegetable Oil | Palm Olein | 10 | 10 | 10 |
| | | Fatty Acid | Fatty Acid (NAA-34) | — | — | — |
| | Hydrophilic Substrate | | Glucose | 10 | 10 | 10 |
| | | | Urea | 0.1 | 0.1 | 0.1 |
| | | | Yeast Extract | 0.25 | 0.25 | 0.25 |
| | Others | | Inorganic Salt | 1.6 | 1.6 | 1.6 |
| | pH Control during Culture | | | Controlled (pH 5) | Controlled (pH 5) | Controlled (pH 5) |

TABLE 6-continued

| | | | Example 3-1 | Example 3-2 | Comparative Example 3-1 |
|---|---|---|---|---|---|
| | | Aerated Agitation Conditions (Amount of Oxygen Supplied to Culture Product) (Apparent $K_La$ (1/hr)) | 226 | 367 | 160 |
| SL-containing Composition | SL Composition (%) | Acidic SL | 18.1 | 17.9 | 5.4 |
| | | Lactonic SL | 79.8 | 80.6 | 94.6 |
| | | Dimeric SL | 2.1 | 1.5 | 0 |
| | | Proportion of Oleic Acid-diacetyl Lactonic SL in Lactonic SL (100%) | 63 | 62.7 | 58.9 |
| | | Water Content (100 - Dry Residue) (%) | 40.5 | 39.4 | 34.9 |
| | | Hexane Extract: Wet-Weight Basis (%) (Dry-Weight Basis (%)) | 0.08 (0.14) | 0.40 (0.66) | 0.36 (0.55) |
| Physical Properties Evaluation | | Viscosity (mPa · s) | 220000 | 221300.0 | ND |
| | Sedimentation Property | Sedimentation Property in Culture Product | ○ | ○ | ○ |
| | | Sedimentation Property in Distilled Water | ○ | ○ | ○ |
| | | Low-temperature Fluidity | ○ | ○ | x |
| | | Result | ○ | ○ | x |

ND: Not Measured

The use of a vegetable oil alone as a hydrophobic substrate with the pH of the culture product controlled to 5 during the culture period, and with oxygen supply in terms of apparent oxygen mass transfer coefficient ($k_La$) set to 160l/hr or lower was confirmed to provide an SL-containing composition that settles well, but that has decreased low-temperature fluidity (Comparative Example 3-1). This indicated that when only a vegetable oil is used as a hydrophobic substrate, setting the amount of oxygen supplied to the culture product in terms of apparent oxygen mass transfer coefficient ($k_La$) to higher than 160 l/hr, preferably 200l/hr or higher while controlling the pH of the culture product to 5 during the culture period is useful in producing an SL-containing composition excellent in handleability in terms of both the sedimentation property and low-temperature fluidity.

Production Example 4: Production of SL-Containing Composition (Production Method 3)

120 mL of a pre-culture broth prepared in the same manner as in Production Example 1 was inoculated into a main culture medium (3 L) in the same manner as in Production Example 1 and subjected to aerated agitation culture at 30° C. for 5 to 10 days (Examples 4-1 to 4-3: 10 days, Comparative Example 4-1: 7 days, Comparative Example 4-2: 5 days) to ferment the broth. The main culture medium for use was prepared by adding the hydrophobic substrate (vegetable oil, fatty acid) and the hydrophilic substrate (glucose, a yeast extract, urea) shown in Table 7 to water to form an aqueous liquid medium containing an inorganic salt (pH before sterilization: 4.5 to 4.8). During the culture period, the pH of the medium was not controlled (the pH decreased to 3 over the course of culture), and the conditions for aerated agitation culture were set such that the amount of oxygen supplied to the medium in terms of apparent oxygen mass transfer coefficient ($k_La$) was the value shown in Table 7 (Example 4-1: aeration volume 0.5 L/min, stirring speed 380 rpm, Example 4-2: aeration volume 0.5 L/min, stirring speed 410 rpm, Example 4-3: aeration volume 0.5 L/min, stirring speed 410 rpm).

On the 6th to 11th day from the start of culture, the culture was ended. In the same manner as in Production Example 1, an SL-containing composition was recovered and obtained. The obtained SL-containing composition was measured for the SL composition (%), the proportion of oleic acid-diacetyl lactonic SL contained in lactonic SL (%), the water content, and the hexane extract content in the same manner as in Production Example 1 according to the methods described above. The obtained SL-containing composition was also evaluated for viscosity (mPa·s), sedimentation property, and low-temperature fluidity according to the methods described above.

Table 7 shows the results collectively.

TABLE 7

| | | | | Example 4-1 | Example 4-2 | Example 4-3 | Comparative Example 4-1 | Comparative Example 4-2 |
|---|---|---|---|---|---|---|---|---|
| Medium & Culture Conditions | Hydrophobic Substrate | Vegetable Oil | Palm Olein | 10 | 10 | 9 | 10 | 10 |
| | | Fatty Acid | Fatty Acid (NAA-34) | — | — | 1 | — | — |
| | Hydrophilic Substrate | Hydrous Glucose | | 10 | 10 | 10 | 10 | 10 |
| | | Urea | | 0.1 | 0.1 | 0.1 | 0.1 | 0.1 |
| | | Yeast Extract | | 0.25 | 0.25 | 0.25 | 0.25 | 0.25 |
| | Others | Inorganic Salt | | 1.6 | 1.6 | 1.6 | 1.6 | 1.6 |
| | pH Control during Culture | | | Not Controlled | Not Controlled | Not Controlled | Not Controlled | Not Controlled |
| | Aerated Agitation Conditions (Amount of Oxygen Supplied to Culture Product) (Apparent $K_La$ (1/hr)) | | | 120 | 145 | 145 | 160 | 540 |
| SL-containing Composition | SL Composition (%) | Acidic SL | | 13.3 | 18.8 | 21.4 | 13.8 | 14.1 |
| | | Lactonic SL | | 77.5 | 55.6 | 64.0 | 43.5 | 18.3 |
| | | Dimeric SL | | 9.2 | 25.7 | 14.6 | 42.7 | 67.6 |

TABLE 7-continued

| | | | Example 4-1 | Example 4-2 | Example 4-3 | Comparative Example 4-1 | Comparative Example 4-2 |
|---|---|---|---|---|---|---|---|
| | Proportion of Oleic Acid-diacetyl Lactonic SL in Lactonic SL (100%) | | 58.9 | 65.4 | 68.6 | 67.3 | 63 |
| | Water Content (100 − Dry Residue) (%) | | 44.4 | 44.5 | 39.7 | 54.4 | 57.5 |
| | Hexane Extract: Wet-Weight Basis (%) | | 0 | 0.56 | 0.25 | 0.23 | 0.050 |
| | (Dry-Weight Basis (%)) | | (0) | (1.01) | (0.41) | (0.51) | (0.12) |
| Physical Properties Evaluation | Viscosity (mPa · s) | | 3220.0 | 3140.0 | 15940 | <36 | 130.7 |
| | Sedimentation Property | Sedimentation Property in Culture Product | ○ | ○ | ○ | x | x |
| | | Sedimentation Property in Distilled Water | ○ | ○ | ○ | x | x |
| | Low-temperature Fluidity | | ○ | ○ | ○ | ○ | ○ |
| | Result | | ○ | ○ | ○ | x | × |

As shown in Production Examples 1 to 3 described above, the use of a vegetable oil alone as a hydrophobic substrate in the medium without pH control of the culture product during the culture period (the initial pH of about 5 decreased to 3 over the course of culture) provides an SL-containing composition with no sedimentation property (Comparative Examples 1-2 to 1-7, and Comparative Example 2-3). In contrast, as shown in Table 7, the use of a vegetable oil alone as a hydrophobic substrate (free fatty acid content: 0%) without pH control of the culture product was confirmed to provide an SL-containing composition with a sedimentation property as well as excellent low-temperature fluidity, if the amount of oxygen supplied to the culture product in terms of apparent oxygen mass transfer coefficient during the culture period is controlled to 145l/hr or lower (Examples 4-1 and 4-2).

In Production Example 1, culture using the medium containing a free fatty acid in an amount of 10% or lower without pH control was confirmed to provide an SL-containing composition with no sedimentation property (Comparative Example 1-1); however, the results of Example 4-3 indicate that in this case as well, an SL-containing composition excellent in both the sedimentation property and low-temperature fluidity can be prepared by setting the amount of oxygen supplied to the culture product in terms of apparent oxygen mass transfer coefficient during the culture period to 145l/hr or lower.

Experiment Example 1: Evaluation of Relationship Between Residual Fatty Acid in Medium and Sedimentation Property of SL In Production Example 1, the relationship between the sedimentation property of SL-containing compositions and the amount of the free fatty acid contained in the compositions (on a dry-weight basis) was evaluated by using SL-containing compositions prepared from the culture system that showed the sedimentation property of an SL-containing composition (Examples 1-3) and the culture system that did not show the sedimentation property of an SL-containing composition (Comparative Example 1-2). The SL-containing composition prepared in Example 1-3 (moisture content: 44.1%) and the SL-containing composition prepared in Comparative Example 1-2 (moisture content: 57.5%) contained a free fatty acid respectively in an amount of 0.36% and 0.117% in terms of a hexane extract amount (on a dry-weight basis).

Specifically, fatty acids were added to the SL-containing compositions obtained in Example 1-3 and Comparative Example 1-2 so as to give the amount (mass %) shown in Table 8. Table 8 also shows the amount of the fatty acid added in terms of a hexane extract amount (on a dry-weight basis). The actual SL-containing compositions each would contain a free fatty acid that corresponds to the amount of a hexane extract in an SL-containing composition determined by adding 0.36% or 0.117% to the value indicated in the "Amount of Fatty Acid Added in Terms of Hexane Extract Amount" column of Table 8.

25 g of distilled water was added to centrifuge tubes containing 5 g of the individual SL-containing compositions to give a total amount of 30 g (water content: 91.7%). These tubes were then shaken by hand at 20° C. for 10 seconds to homogeneously mix them and allowed to stand for 5 minutes, followed by evaluating the sedimentation property (whether sediment is present). The method for evaluating the sedimentation property was performed according to the following criteria.

Evaluation of Sedimentation Property

○: Sedimentation (sediment) was observed within 5 minutes after the tube was allowed to stand.

x: No sedimentation (sediment) was observed within 5 minutes after the tube was allowed to stand.

Table 8 summarizes the results.

TABLE 8

(1)

| | Example SL-containing Composition (Example 1-3) Used: Dry Residue: 55.9%, Hexane Extract Amount: 0.36% | | | | | | | | | | | | | |
|---|---|---|---|---|---|---|---|---|---|---|---|---|---|---|
| | 5-1 | 5-2 | 5-3 | 5-4 | 5-5 | 5-6 | 5-7 | 5-8 | 5-9 | 5-10 | 5-11 | 5-12 | 5-13 | 5-14 |
| Amount of Fatty Acid Added in Terms of Hexane Extract Amount | 2.3<br>(2.66) | 3.4<br>(3.76) | 4.5<br>(4.86) | 5.6<br>(5.96) | 6.6<br>(6.96) | 7.6<br>(7.96) | 8.6<br>(3.96) | 9.6<br>(9.96) | 10.5<br>(10.86) | 11.5<br>(11.86) | 12.4<br>(12.76) | 13.3<br>(13.66) | 14.5<br>(14.86) | 20.0<br>(20.36) |

TABLE 8-continued

| | | | | | | | | | | | | | | | |
|---|---|---|---|---|---|---|---|---|---|---|---|---|---|---|---|
| n-Hexanoic Acid | C6:0 | ○ | ○ | ○ | ○ | ○ | ○ | ○ | ○ | ○ | ○ | ○ | ○ | ○ | ○ |
| n-Octanoic Acid | C8:0 | ○ | ○ | ○ | ○ | ○ | ○ | ○ | ○ | ○ | ○ | ○ | ○ | ○ | ○ |
| Oleic Acid | C18:1 | ○ | ○ | ○ | ○ | ○ | ○ | ○ | ○ | ○ | ○ | ○ | ○ | ○ | ○ |
| Linoleic Acid | C18:2 | ○ | ○ | ○ | ○ | ○ | ○ | ○ | ○ | ○ | ○ | ○ | ○ | ○ | ○ |
| [α-Linolenic Acid | C18:3 | ○ | ○ | ○ | ○ | ○ | ○ | ○ | ○ | ○ | ○ | ○ | ○ | ○ | ○ |

(2)

| | | Reference Example SL-containing Composition (Comparative Example 1-2) Used: Dry Residue: 42.5%, Hexane Extract Amount: 0.117% | | | | | | | | | | | | | |
|---|---|---|---|---|---|---|---|---|---|---|---|---|---|---|---|
| | | 5-1 | 5-2 | 5-3 | 5-4 | 5-5 | 5-6 | 5-7 | 5-8 | 5-9 | 5-10 | 5-11 | 5-12 | 5-13 | 5-14 |
| Amount of Fatty Acid Added in Terms of Hexane Extract Amount | | 2.3 (2.417) | 3.4 (3.517) | 4.5 (4.617) | 5.6 (5.717) | 6.6 (6.717) | 7.6 (7.717) | 8.6 (8.717) | 9.6 (9.717) | 10.5 (10.617) | 11.5 (11.617) | 12.4 (12.517) | 13.3 (13.417) | 14.5 (14.617) | 20.0 (20.117) |
| n-Hexanoic Acid | C6:0 | x | x | x | x | x | ○ | ○ | ○ | ○ | ○ | ○ | ○ | ○ | ND |
| n-Octanoic Acid | C8:0 | x | x | x | x | x | ○ | ○ | ○ | ○ | ○ | ○ | ○ | ○ | ND |
| Oleic Acid | C18:1 | x | x | ○ | ○ | ○ | ○ | ○ | ○ | ○ | ○ | ○ | ○ | ○ | ○ |
| Linoleic Acid | C18:2 | x | x | x | x | x | ○ | ○ | ○ | ○ | ○ | ○ | ○ | ○ | ND |
| α-Linolenic Acid | C18:3 | x | x | x | x | ○ | ○ | ○ | ○ | ○ | ○ | ○ | ○ | ○ | ND |

ND: Not Performed

The results of Table 8 (1) indicate that the SL-containing composition obtained in Example 1-3 (i.e., the SL-containing composition with the content of lactonic SL and oleic acid-diacetyl lactonic SL satisfying requirements (A) and (B) of the present invention) was confirmed to have an excellent sedimentation property and good handleability regardless of the amount of the fatty acid (the content of a hexane extract). However, the results of Table 8 (2) indicate that the SL-containing composition obtained in Comparative Example 1-2 (i.e., the SL-containing composition with the content of lactonic SL not satisfying requirement (A) of the present invention) was confirmed to have a poor sedimentation property and poor handleability, depending the type of the fatty acid though, when the amount of the fatty acid is 7% or lower, particularly 6% or lower, in terms of the amount of a hexane extract. This indicates that the technique of the present invention is particularly useful for SL-containing compositions with a fatty acid content of 7% or lower, particularly 6% or lower, in terms of the content of a hexane extract, which are SL-containing compositions having a tendency to have a poor sedimentation property.

Experiment Example 2: Evaluation of Effect of Free Fatty Acid Content in SL-Containing Composition on Foaming Power SL-containing compositions containing a free fatty acid in different amounts were individually added to a dish detergent. The foaming power of each dish detergent was evaluated, and the effect of the free fatty acid content in the SL-containing compositions on foaming power was evaluated.

(1) Preparation of Test Sample

SL-containing compositions 1 to 4 containing a fatty acid in the amounts shown in Table 9 were prepared from the SL-containing composition of Example 1-3 and oleic acid. As shown in Table 10, 0.5 g of these SL-containing compositions 1 to 4 were individually added to 4.5 g of a dish detergent (Happy Elephant, vegetable and dish detergent (Saraya Co., Ltd.); fatty acid content: 0%), thereby preparing test samples 1 to 4.

TABLE 9

| No. | Amount of Fatty Acid Added (%) | Proportion of Fatty Acid Added in Composition (%) (Dry-Weight Basis) | Total Amount of Fatty Acid in Composition (%) (Dry-Weight Basis) |
|---|---|---|---|
| SL-containing Composition 1 | SL-containing Composition* + 0% Fatty Acid | 0 | 0.36 |
| SL-containing Composition 2 | SL-containing Composition* + 3% Fatty Acid | 2.68 | 3.04 |
| SL-containing Composition 3 | SL-containing Composition* + 6% Fatty Acid | 5.37 | 5.73 |
| SL-containing Composition 4 | SL-containing Composition* + 9% Fatty Acid | 8.05 | 8.41 |

Note:
*SL-containing Composition: Example 1-3 (Hexane Extract 0.36%, Dry Residue 55.9%)
Fatty Acid: Fatty Acid (NAA-34)

(2) Evaluation Method for Foaming Power

The prepared test samples 1 to 4, and a dish detergent (control sample) were diluted with distilled water to give a dish detergent concentration of 15%.

The diluted test samples 1 to 4 and the control sample in an amount of 1 g each were individually added to a measuring cylinder, and 100 mL of tap water (25° C.) was added thereto, followed by agitation at 5000 rpm for 3 minutes with a Robomix having a homogenizing disperser (diameter 40) attached (model: RM/1001, manufacturer: PRIMIX Corporation).

The height of foam after 30 seconds, 60 seconds, and 180 seconds from the end of agitation was read from the scale on the measuring cylinder.

(3) Evaluation Results of Foaming Power

Table 10 shows the results.

TABLE 10

| Specimen | Sample | Height of Foam after Each Standing Time (mL) | | |
|---|---|---|---|---|
| | | 30 s | 60 s | 180 s |
| Control | Dish Detergent | 280 | 260 | 215 |
| 1 | Dish Detergent + SL-containing Composition 1 | 370 | 350 | 300 |
| 2 | Dish Detergent + SL-containing Composition 2 | 310 | 285 | 250 |
| 3 | Dish Detergent + SL-containing Composition 3 | 260 | 240 | 215 |
| 4 | Dish Detergent + SL-containing Composition 4 | 240 | 210 | 180 |

The results shown in Table 10 indicate that the SL-containing composition according to the present invention added to the dish detergent increased the foaming power (see the control sample and test sample 1). The results also indicate that the increase in foaming power is limited with the increase in the fatty acid content in the SL-containing composition (test samples 1 to 4). Limiting the fatty acid content in the SL-containing composition to 6% or lower leads to a foaming power of the SL-containing composition equivalent to or greater than the foaming power of the dish detergent itself. Thus, the free fatty acid content in the SL-containing composition appears to be preferably 6% or lower also from the viewpoint of foaming properties.

The invention claimed is:

1. A method for producing a sophorolipid-containing composition comprising the following characteristics (A) to (C):

(A) the content of lactonic sophorolipid being 45 to 81 mass % of the total amount of the sophorolipid taken as 100 mass %, (B) the content of oleic acid-diacetyl lactonic sophorolipid being 95 mass % or lower of the total amount of the lactonic sophorolipid taken as 100 mass %, and (C) the content of a hexane extract being 6 mass % or lower on a dry-weight basis;

the method comprising culturing a sophorolipid-producing yeast in a medium containing a hydrophobic substrate and a hydrophilic substrate, wherein the hydrophobic substrate is a fatty acid and does not contain a vegetable oil, a culture product at an early stage of culture has a pH of 4 to 5, the pH of the culture product is not controlled during a culture period, and conditions for aerated agitation culture during the culture period are set such that the amount of oxygen supplied to the culture product in terms of apparent oxygen mass transfer coefficient ($k_La$) is 145 1/hr or higher.

2. A method for producing a sophorolipid-containing composition comprising the following characteristics (A) to (C):

(A) the content of lactonic sophorolipid being 45 to 81 mass % of the total amount of the sophorolipid taken as 100 mass %, (B) the content of oleic acid-diacetyl lactonic sophorolipid being 95 mass % or lower of the total amount of the lactonic sophorolipid taken as 100 mass %, and (C) the content of a hexane extract being 6 mass % or lower on a dry-weight basis;

the method comprising culturing a sophorolipid-producing yeast in a medium containing a hydrophobic substrate and a hydrophilic substrate, wherein the hydrophobic substrate is a vegetable oil with a melting point of 30° C. or lower, the pH of a culture product during a culture period is adjusted to 4.5 to 5, and conditions for aerated agitation culture during the culture period are set such that the amount of oxygen supplied to the culture product in terms of apparent oxygen mass transfer coefficient ($k_La$) is 200 1/hr or higher.

3. A method for producing a sophorolipid-containing composition comprising the following characteristics (A) to (C):

(A) the content of lactonic sophorolipid being 45 to 81 mass % of the total amount of the sophorolipid taken as 100 mass %, (B) the content of oleic acid-diacetyl lactonic sophorolipid being 95 mass % or lower of the total amount of the lactonic sophorolipid taken as 100 mass %, and (C) the content of a hexane extract being 6 mass % or lower on a dry-weight basis;

the method comprising culturing a sophorolipid-producing yeast in a medium containing a hydrophobic substrate and a hydrophilic substrate, wherein the hydrophobic substrate is a vegetable oil with a melting point of 30° C. or lower, a culture product at an early stage of culture has a pH of 4 to 5, the pH of the culture product is not controlled during a culture period, and conditions for aerated agitation culture during the culture period are set such that the amount of oxygen supplied to the culture product in terms of apparent oxygen mass transfer coefficient (kLa) is 145 l/hr or lower.

4. A method for producing a sophorolipid-containing composition comprising the following characteristics (A) to (C):

(A) the content of lactonic sophorolipid being 45 to 81 mass % of the total amount of the sophorolipid taken as 100 mass %, (B) the content of oleic acid-diacetyl lactonic sophorolipid being 95 mass % or lower of the total amount of the lactonic sophorolipid taken as 100 mass %, and (C) the content of a hexane extract being 6 mass % or lower on a dry-weight basis;

the method comprising culturing a sophorolipid-producing yeast in a medium containing a hydrophobic substrate and a hydrophilic substrate, wherein the hydrophobic substrate contains a vegetable oil with a melting point of 30° C. or lower and a fatty acid, the proportion of a free fatty acid is 20 mass % or higher of the total amount of the vegetable oil with a melting point of 30° C. or lower and the fatty acid taken as 100 mass % contained in the medium, a culture product at an early stage of culture has a pH of 4 to 5, the pH of the culture product is not controlled during a culture period, and conditions for aerated agitation culture during the culture period are set such that the amount of oxygen supplied to the culture product in terms of apparent oxygen mass transfer coefficient ($k_L a$) is 145 l/hr or higher.

* * * * *